US010751387B2

(12) United States Patent
Sun et al.

(10) Patent No.: US 10,751,387 B2
(45) Date of Patent: Aug. 25, 2020

(54) PHARMACOLOGICAL THERAPY FOR NEURONOPATHIC GAUCHER DISEASE

(71) Applicant: Children's Hospital Medical Center, Cincinnati, OH (US)

(72) Inventors: Ying Sun, Mason, OH (US); Benjamin Liou, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 92 days.

(21) Appl. No.: 15/497,789

(22) Filed: Apr. 26, 2017

(65) Prior Publication Data

US 2017/0319651 A1 Nov. 9, 2017

Related U.S. Application Data

(60) Provisional application No. 62/332,178, filed on May 5, 2016.

(51) Int. Cl.
*A61K 31/395* (2006.01)
*A61K 38/17* (2006.01)

(52) U.S. Cl.
CPC .......... *A61K 38/177* (2013.01); *A61K 31/395* (2013.01); *G01N 2800/04* (2013.01); *G01N 2800/7085* (2013.01)

(58) Field of Classification Search
CPC .................................................. A61K 38/177
See application file for complete search history.

(56) References Cited

PUBLICATIONS

Adasme, T., et al., "Involvement of ryanodine receptors in neurotrophin-induced hippocampal synaptic plasticity and spatial memory formation," Proc. Natl. Acad. Sci. U S A., 2011, 108:3029-3034, 6 pgs.
Alonso, M.T, et al., "Fura-2 antagonises calcium-induced calcium release," Cell Calcium, 2003, 33:27-35, 9 pgs.
Ashe, K.M., et al., "Iminosugar-based inhibitors of glucosylceramide synthase increase brain glycosphingolipids and survival in a mouse model of Sandhoff disease," PLoS One, 2011, 6(6):e21758, 11 pgs.
Bading, H., et al., "Regulation of gene expression in hippocampal neurons by distinct calcium signaling pathways," Science. 1993, 260:181-186, 8 pgs.
Balaban, R.S., "The role of $Ca^{2+}$ signaling in the coordination of mitochondrial ATP production with cardiac work," Biochim. Biophys. Acta., 2009, 1787:1334-1341, 20 pgs.
Bito, H., et al., "CREB Phosphorylation and Dephosphorylation: a $Ca^{2+}$—and Stimulus Duration-Dependent Switch for Hippocampal Gene Expression," Cell, 1996, 87:1203-1214, 12 pgs.
Bouchard, R., et al., "Presence and functional significance of presynaptic ryanodine receptors," Prog. Neurobiol, 2003, 69:391-418, 28 pgs.
Bround, M.J., et al., "Cardiomyocyte ATP Production, Metabolic Flexibility, and Survival Require Calcium Flux Through Cardiac Ryanodine Receptors in Vivo," J. Biol. Chem, 2013, 288(26):18975-18986, 12 pgs.
Burrow, T.A., et al. "CNS, lung, and lymph node involvement in Gaucher disease type 3 after 11years of therapy: Clinical, histopathologic, and biochemical findings," Mol. Genet. Metab, 2015, 114:233-241, 9 pgs.
Cabrera-Salazar, M.A. et al., "Systemic Delivery of a Glucosylceramide Synthase Inhibitor Reduces CNS Substrates and Increases Lifespan in a Mouse Model of Type 2 Gaucher Disease," PLoS One, 2012, 7(8):e43310, 9 pgs.
Chakroborty, S., et al., "Stabilizing ER $Ca^{2+}$ Channel Function as an Early Preventative Strategy for Alzheimer's Disease," PLoS One, 2012, 7:e52056, 12 pgs.
Chen, X., et al., "Dantrolene is neuroprotective in Huntington's disease transgenic mouse model," Mol. Neurodegener, 2011, 6:81, 12 pgs.
Chow, F.A., et al., "The Autonomous Activity of Caleium/Calmodulin-Dependent Protein Kinase IV is Required for Its Role in Transcription," J. Biol. Chem., 2005, 280:20530-20538, 9 pgs.
Cleeter, M.W.J., et al., "Glucocerebrosidase inhibition causes mitochondrial dysfunction and free radical damage," Neurochem. Int., 2013, 62:1-7, 7 pgs.
Conradi, N.G., et al., "Neuropathology of the Norrbottnian Type of Gaucher Disease: Morphological and Biochemical Studies," Acta Neuropathol., 1984, 65:99-109, 11 pgs.
Dasgupta, N., et al., "Neuronopathie Gaucher disease: dysregulated mRNAs and miRNAs in brain pathogenesis and effects of pharmacologic chaperone treatment in a mouse model," Hum. Mol. Genet., 2015, 24(4):7031-7048, 18 pgs.
Del Prete, D., et al., "Ryanodine receptors: physiological function and deregulation in Alzheimer disease," Mol. Neurodegener., 2014, 9:21, 15 pgs.
Denton, R.M., "Regulation of mitochondrial dehydrogenases by calcium ions," Biochim. Biophys. Acta., 2009, 1787:1309-1316, 8 pgs.
Elrick, M.J., et al., "Impaired proteolysis underlies autophagic dysfunction in Niemann-Pick type C disease," Hum. Mol. Genet., 2012, 21(22):4876-4887, 12 pgs.
Enokizono, J., et al., "Quantitative Investigation of the Role of Breast Cancer Resistance Protein (Bcrp/Abcg2) in Limiting Brain and Testis Penetration of Xenobiotic Compounds," Drug Metab. Dispos., 2008, 36(6):995-1002, 8 pgs.
Ferreiro, E., et al., "Involvement of Endoplasmic Reticulum $Ca^{2+}$ Release Through Ryanodine and Inositol 1,4,5-Triphosphate Receptors in the Neurotoxic Effects Induced by the Amyloid-β Peptide," J. Neurosci. Res., 2004, 76:872-880, 9 pgs.
Fleming, S.M., et al., "Early and Progressive Sensorimotor Anomalies in Mice Overexpressing Wild-Type Human α-Synuclein," J. Neurosci., 2004, 24(42):9434-9440, 7 pgs.
Fruen, B.R., et al., "Differential $Ca^{2+}$ sensitivity of skeletal and cardiac muscle ryanodine receptors in the presence of calmodulin," Am. J. Physiol. Cell Physiol., 2000, 279:C724-733, 10 pgs.
Fruen, B.R., et al., "Dantrolene Inhibition of Sarcoplasmic Reticulum $Ca^{2+}$ Release by Direct and Specific Action at Skeletal Muscle Ryanodine Receptors," J. Biol. Chem., 1997, 272(43):26965-26971, 7 pgs.

(Continued)

*Primary Examiner* — Robert C Hayes
(74) *Attorney, Agent, or Firm* — Frost Brown Todd LLC; Nicole M. Tepe

(57) ABSTRACT

The instant disclosure relates to methods and compositions for the treatment of Gaucher disease, particularly type II and III neuronopathic Gaucher disease (nGD). The methods include the step of administering to an individual in need thereof an effective amount of a ryanodine receptor inhibitor or a pharmaceutically acceptable salt thereof.

17 Claims, 14 Drawing Sheets

(56) References Cited

PUBLICATIONS

Furuichi, T., et al., "Multiple Types of Ryanodine Receptor/Ca$^{2+}$ Release Channels are Differentially Expressed in Rabbit Brain," J. Neurosci., 1994, 14(8):4794-4805, 12 pgs.

Gennaro, A.R., Ed., *Remington's Pharmaceutical Sciences*, 18th Ed., Mack Publ. Co., Easton, PA, 1990, 8 pgs, Table of contents only.

Ghislat, G., et al., "Withdrawal of Essential Amino Acids Increases Autophagy by a Pathway Involving Ca$^{2+}$/Calmodulin-dependent Kinase Kinase-β (CaMKK-β)," J. Biol. Chem., 2012, 287(46):38625-38636, 12 pgs.

Giannini, G., et al., "Molecular Structure and Tissue Distribution of Ryanodine Receptors Calcium Channels," Med. Res. Rev., 1995, 15(4):313-323, 11 pgs.

Ginzburg, L. et al., "Defective calcium homeostasis in the cerebellum in a mouse model of Niemann-Pick A disease," J. Neurochem., 2005, 95:1619-1628, 10 pgs.

Grabowski, G.A., et al., "146: Gaucher Disease," The Online Metabolic and Molecular Bases of Inherited Diseases, (eds. Valle, D., Beaudet, A., Vogelstein, B., Kinzler, K.W., Antonarakis, S.E., Ballabio, A., Scriver, C.R., Sly, W.S., Childs, B., Bunz, F., Gibson, K.M. and Mitchell, G.), The McGraw-Hill Companies, Inc., New York, 2010, 107 pgs.

Grotemeier, A., et al., "AMPK-independent induction of autophagy by cytosolic Ca$^{2+}$ increase," Cell Signal, 2010, 22:914-925, 12 pgs.

Jennings, J.J., Jr., et al., "Mitochondrial Aberrations in Mucolipidosis Type IV," J. Biol. Chem., 2006, 281(51):39041-39050, 10 pgs.

Kaye, E.M., et al., "Type 2 and Type 3 Gaucher Disease: A Morphological and Biochemical Study," Ann. Neurol., 1986, 20(2):223-230, 8 pgs.

Kilpatrick, B.S., et al., "Endoplasmic reticulum and lysosomal Ca$^{2+}$ stores are remodelled in GBA1-linked Parkinson disease patient fibroblasts," Cell Calcium, 2015, 59:12-20, 9 pgs.

Kiselyov, K., et al., "Aberrant Ca$^{2+}$ handling in lysosomal storage disorders," Cell Calcium, 2010, 47:103-111, 9 pgs.

Klegeris A., et al., "Functional Ryanodine Receptors Are Expressed by Human Microglia and THP-1 Cells: Their Possible Involvement in Modulation of Neurotoxicity," J Neurosci Res., Aug. 1, 2007, 85(10):2207-15, 9 pgs.

Korkotian, E., et al., "Elevation of Intracellular Glucosylceramide Levels Results in an Increase in Endoplasmic Reticulum Density and in Functional Calcium Stores in Cultured Neurons," J. Biol. Chem., 1999, 274(31):21673-21678, 6 pgs.

Krause, T., et al., "Dantrolene—A review of its pharmacology, therapeutic use and new developments," Anaesthesia, 2004, 59:364-373, 10 pgs.

Kuter, D.J., et al., "Miglustat therapy in type 1 Gaucher disease: Clinical and safety outcomes in a multicenter retrospective cohort study," Blood Cells Mol. Dis., 2013, 51: 116-124, 9 pgs.

Lim, J-A., et al., "Defects in calcium homeostasis and mitochondria can be reversed in Pompe disease," Autophagy, 2015, 11(2):385-402, 18 pgs.

Liou, B., et al., "Analyses of Valiant Acid β-glucosidases: *Effects of Gaucher Disease Mutations*," J. Biol. Chem., 2006, 281(7):4242-4253, 12 pgs.

Lloyd-Evans, E., et al., "Niemann-Pick disease type C1 is a sphingosine storage disease that causes deregulation of lysosomal calcium," Nat. Med., 2008, 14(11):1247-1255, 10 pgs.

Lukina, E., et al., "Eliglustat, an investigational oral therapy for Gaucher disease type 1: Phase 2 trial results after 4 years of treatment," Blood Cells Mol. Dis., 2014, 53:274-276, 3 pgs.

Malik, Z.A., et al., "Mission CaMKIIγ: Shuttle Calmodulin from Membrane to Nucleus," Cell, 2014, 159:235-237, 3 pgs.

Marshall, J., et al., "CNS-accessible Inhibitor of Glucosylceramide Synthase for Substrate Reduction Therapy of Neuronopathic Gaucher Disease," Mol. Ther., 2016, 24(6):1019-1029, 11 pgs.

Mazzulli, J.R., et al., "Gaucher's Disease Glucocerebrosidase and α-synuclein form a bidirectional pathogenic loop in synucleinopathies," Cell, 2011, 146(1):37-52, 28 pgs.

Mbaya, E., et al., "Calcium signalling-dependent mitochondrial dysfunction and bioenergetics regulation in respiratory chain Complex II deficiency," Cell Death Differ., 2010, 17:1855-1866, 12 pgs.

Mehra, D., et al., "Multiple Modes of Ryanodine Receptor 2 Inhibition by Flecainide," Mol Pharmacol., Dec. 2014, 86(6):696-706, 11 pgs.

Mu, T.-W., et al., "Partial Restoration of Mutant Enzyme Homeostasis in Three Distinct Lysosomal Storage Disease Cell Lines by Altering Calcium Homeostasis," PLoS Biol., 2008, 6(2):e26, 13 pgs.

Muehlschlegel, S. et al., "Dantrolene: mechanisms of neuroprotection and possible clinical applications in the neurointensive care unit," Neurocrit. Care., 2009, 10(1):103-115, 19 pgs.

Nietupski, J.B., et al., "Iminosugar-based inhibitors of glucosylceramide synthase prolong survival but paradoxically increase brain glucosylceramide levels in Niemann-Pick C mice," Mol. Genet. Metab., 2012, 105:621-628, 8 pgs.

Nilsson, O., et al., "Accumulation of Glucosylceramide and Glucosylsphingosine (Psychosine) in Cerebrum and Cerebellum in Infantile and Juvenile Gaucher Disease," J. Neurochem., 1982, 39:709-718, 6 pgs.

Ong, D.S., et al., "Endoplasmic Reticulum Ca$^{2+}$ Increases Enhance Mutant Glucocerebrosidase Proteostasis," Nat. Chem. Biol., 2010, 6(6):424-432, 22 pgs.

Orvisky, E., et al., "Glucosylsphingosine accumulation in tissues from patients with Gaucher disease: correlation with phenotype and genotype," Mol. Genet. Metab., 2002, 76:262-270, 9 pgs.

Osellame, L.D. et al., "Defective quality control mechanisms and accumulation of damaged mitochondria link Gaucher and Parkinson diseases," Autophagy, 2013, 9(10):1633-1635, 3 pgs.

Osellame, L.D., et al., "Mitochondria and Quality Control Defects in a Mouse Model of Gaucher Disease—Links to Parkinson's Disease," Cell Metab., 2013, 17:941-953, 13 pgs.

Ostrovskaya, O., et al., "Inhibition of Ryanodine Receptors by 4-(2-Aminopropyl)-3,5-dichloro-N,N-dimethylaniline (FLA 365) in Canine Pulmonary Arterial Smooth Muscle Cells," Journal of Pharmacology and Experimental Therapeutics, Oct. 2007, 323(1):381-390, 10 pgs.

Oules, B., et al., "Ryanodine receptor blockade reduces amyloid-beta load and memory impairments in Tg2576 mouse model of Alzheimer disease," J. Neurosci., 2012, 32(34):11820-11834, 38 pgs.

Ozawa, T., "Modulation of ryanodine receptor Ca$^{2+}$ channels (Review)," Mol. Med. Rep., 2010, 3:199-204, 6 pgs.

Pelled, D., et al., "Inhibition of Calcium Uptake via the Sarco/Endoplasmic Reticulum Ca$^{2+}$-ATPase in a Mouse Model of Sandhoff Disease and Prevention by Treatment with N-Butyldeoxynojirimycin," J. Biol. Chem., 2003, 278(32):29496-29501, 6 pgs.

Pelled, D., et al., "Enhanced calcium release in the acute neuronopathic form of Gaucher disease," Neurobiol. Dis., 2005, 18:83-88, 6 pgs.

Popescu, B.O., et al., "Dantrolene protects neurons against kainic acid induced apoptosis in vitro and in vivo," J. Cell Mol. Med., 2002, 6(4):555-569, 15 pgs.

Rigat, B. et al., "Diltiazem, a L-type Ca$^{2+}$ channel blocker, also acts as a pharmacological chaperone in Gaucher patient cells," Mol. Genet. Metab., 2009, 96(4):225-232, 18 pgs.

Rogers, G.W., et al., "High Throughput Microplate Respiratory Measurements Using Minimal Quantities of Isolated Mitochondria," PLoS One, 2011, 6(7):e21746, 12 pgs.

Sawkar, A.R., et al., "Gaucher Disease-Associated Glucocerebrosidases Show Mutation-Dependent Chemical Chaperoning Profiles," Chem. Biol., 2005, 12:1235-1244, 10 pgs.

Schindelin, J., et al., "Fiji—an Open Source platform for biological-image analysis," Nat. Methods, 2012, 9(7):676-682, 15 pgs.

Schondorf, D.C., et al., "iPSC-derived neurons from GBA1-associated Parkinson's disease patients show autophagic defects and impaired calcium homeostasis," Nat. Commun., 2014, 5:4028, 17 pgs.

Schultheis, P.J., et al., "Atp13a2-deficient mice exhibit neuronal ceroid lipofuscinosis, limited α-synuclein accumulation and age-dependent sensorimotor deficits," Hum. Mol. Genet., 2013, 22(10):2067-2082, 16 pgs.

(56) References Cited

PUBLICATIONS

Settembre, C., et al., "A block of autophagy in lysosomal storage disorders," Hum. Mol. Genet., 2008, 17(1):119-129, 11 pgs.

Soderling, T.R., "The $Ca^{2+}$-calmodulin-dependent protein kinase cascade," Trends Biochem. Sci., 1999, 24:232-236, 5 pgs.

Sun, Y., et al., "Impaired autophagosomes and lysosomes in neuronopathic Gaucher disease," Autophagy, 2010, 6(5):648-649, 2 pgs.

Sun, Y., et al., "In Vivo and Ex Vivo Evaluation of L-Type Calcium Channel Blockers on Acid β-Glucosidase in Gaucher Disease Mouse Models," PLoS One, 2009, 4(10):e7320, 8 pgs.

Sun, Y., et al., "Neuronopathic Gaucher disease in the mouse: viable combined selective saposin C deficiency and mutant glucocerebrosidase (V394L) mice with glucosylsphingosine and glucosylceramide accumulation and progressive neurological deficits," Hum. Mol. Genet., 2010, 19(6):1088-1097, 10 pgs.

Sun, Y., et al., "Gaucher disease mouse models: point mutations at the acid β-glucosidase locus combined with low-level prosaposin expression lead to disease variants," J. Lipid Res., 2005, 46:2102-2113, 12 pgs.

Sun, Y., et al., "Isofagomine In Vivo Effects in a Neuronopathic Gaucher Disease Mouse," PLoS One, 2011, 6(4):e19037, 12 pgs.

Sun, Y., et al., "Substrate Compositional Variation with Tissue/Region and Gba1 Mutations in Mouse Models—Implications for Gaucher Disease," PLoS One, 2013, 8(3):e57560, 14 pgs.

Tantawy, A.A., et al., "Evoked potentials and neurocognitive functions in pediatric Egyptian Gaucher patients on enzyme replacement therapy: a single center experience," J. Inherit. Metab. Dis., 2013, 36:1025-1037, 13 pgs.

Tremblay, R.G., et al., "Differentiation of mouse Neuro 2A cells into dopamine neurons," J. Neurosci. Methods, 2010, 186:60-67, 8 pgs.

Vitner, E.B., et al., "RIPK3 as a potential therapeutic target for Gaucher's disease," Nat. Med., 2014, 20(2):204-208, 6 pgs.

Wang, F., et al., "$Ca^{2+}$ Homeostasis Modulation Enhances the Amenability of L444P Glucosylcerebrosidase to Proteostasis Regulation in Patient-Derived Fibroblasts," ACS Chem. Biol., 2011, 6:158-168, 11 pgs.

Wehrens, X.H.T., et al., "Protection from Cardiac Arrhythmia Through Ryanodine Receptor-Stabilizing Protein Calstabin2," Science, 2004, 304(5668):292-6, 5 pgs.

Williams, I.M., et al., "Improved neuroprotection using miglustat, curcumin and ibuprofen as a triple combination therapy in Niemann-Pick disease type C1 mice," Neurobiol. Dis., 2014, 67:9-17, 9 pgs.

Wong, K., et al., "Neuropathology provides clues to the pathophysiology of Gaucher disease," Mol. Genet. Metab., 2004, 82:192-207, 16 pgs.

Xu, Y.H., et al., "Dependence of reversibility and progression of mouse neuronopathic Gaucher disease on acid β-glucosidase residual activity levels," Mol. Genet. Metab., 2008, 94:190-203, 14 pgs.

Xu, Y.H., et al., "Multiple pathogenic proteins implicated in neuronopathic Gaucher disease mice," Hum. Mol. Genet., 2014, 23(15):3943-3957, 15 pgs.

Yu, T., et al., "Ryanodine receptor antagonists adapt NPC1 proteostasis to ameliorate lipid storage in Niemann-Pick type C disease fibroblasts," Hum. Mol. Genet., 2012, 21(14):3205-3214, 10 pgs.

Zhang, X., et al., "Genome-wide analysis of cAMP-response element binding protein occupancy, phosphorylation, and target gene activation in human tissues," Proc. Natl. Acad. Sci. U S A., 2005, 102(12):4459-4464, 6 pgs.

U.S. Appl. No. 62/332,178, filed May 5, 2016.

CD 68

A

B

PHARMACOLOGICAL THERAPY FOR NEURONOPATHIC GAUCHER DISEASE

CROSS REFERENCE TO RELATED APPLICATIONS

This application claims the benefit of and priority to U.S. 62/332,178, to Sun et al., filed on May 5, 2016, the contents of which are incorporated by reference in their entirety for all purposes.

BACKGROUND

Treatment of genetic brain disorders including neurodegenerative diseases are an unmet medical need. These include rare, lysosomal storage diseases, and more common diseases such as Parkinson's disease. Neurodegenerative diseases strike about 50 million Americans each year, demanding enormous cost in medical expenses and lost productivity. Currently, there is no effective treatment for neurodegenerative diseases and there is a need for such in the art. The instant disclosure seeks to address one or more of the aforementioned needs in the art.

BRIEF SUMMARY

Disclosed are methods and compositions for the treatment of Gaucher disease, particularly type II and III neuronopathic Gaucher disease (nGD). The methods include the step of administering to an individual in need thereof an effective amount of a ryanodine receptor inhibitor or a pharmaceutically acceptable salt thereof.

BRIEF DESCRIPTION OF THE DRAWINGS

(FIG. 1A) Decreased mRNA expression (fold change of WT level) of three Ryrs in 4L;C* brain regions determined by RNASeq analysis (n=3 mice/group). (FIG. 1B) Immunoblot of brain lysate showed Ryr3 was expressed at normal levels at 13 days of age and significantly decreased by 44 days of age in 4L;C* brain (27% of WT level) compared to WT mice. P-values were from Student's t-test, n=3 mice/group, 2-4 replicates of the experiment. (FIG. 1C) Immunofluorescence staining of brain sections by anti-Ryr1 and anti-Ryr3 antibodies (green) showed decreased Ryr signals in 4L;C* brain including cortex and midbrain regions. Scale bar is 20 μm for all the images. (FIG. 1D) Co-staining of Ryr3 (green) with neural cell markers. NeuN (red) is for neurons. GFAP (red) is for astrocytes. 04 (red) is for oligodendrocytes. Ryr3 signals were detected in neurons, astrocytes and oligodendrocytes in WT midbrains. 4L;C* midbrain had low level of Ryr 3 signals in those cells compared to WT. Scale bar is 20 μm for all the images. DAPI (blue) stained cell nuclei. Images are representative from n=3 mice for each genotype.

(FIG. 3A) Gait analysis. Left stride (Left panel), right stride (Middle panel), base width (Right panel). The mice were subjected to two to three tests at 30 and 40 days of age. Dantrolene (Dan) treatment significantly increased left and right strides in 4L;C* mice at 40 days of age, and reduced base width at both 30 and 40 days of age compared to untreated 4L;C* mice. Littermate (4L;WT) mice that have no phenotype were used as normal controls in the analysis. Data were analysed by Student's t-test. (FIG. 3B) Life span. The survival rate of dantrolene treated 4L;C* mice (blue) was significantly increased compared to untreated 4L;C* mice (orange). Median survival days is 50 days or 44 days for treated or untreated 4L;C* mice, respectively. The life span of dantrolene treated 4L;C* mice was prolonged by 12.3%. Littermate (4L;WT) control mice (black) had normal life span. Data are presented as Kaplan-Meier curve analysed by Mantel-Cox test. (FIG. 3C) CNS-inflammation. Positive CD68 staining (brown) in microglial cells indicate inflammation in 4L;C* brain. Compared to untreated 4L;C, the CD68 signal was significantly reduced in dan-trolene treated 4L;C* brains. The representative image for each group is shown. CD68 signal intensity in brain sections was quantitated by NIH image J and presented as % of untreated 4L;C* level. P-value was from Student's t-test (n=2-3 mice/group). (FIG. 3D) Mitochondrial ATP production rate. 4L;C. brain had 37% of ATP production rate (pmol/min/mg mitochondrial protein) compared to WT brains. Dantrolene treatment on 4L;C* mice improved ATP production to 77% of WT level. One-way ANOVA with post-hoc Tukey test (P<0.05), n=3 mice/group, 6 replicates/sample/assay, duplicate assays. (FIG. 3E) Immunoblot of LC3. LC3-II is barely detectable in WT brain. LC3-II levels were increased in 4L;C. cerebrum compared to WT. Dantrolene treated 4L;C* cerebrum showed significantly reduced level of LC3-II compared to untreated 4L;C*. One-way ANOVA with post-hoc Tukey test (P<0.05), n=3 mice/group, duplicate experiments.

(FIG. 4A) Compared to WT cortex, cerebellum, midbrain and brain stem, 4L;C* mice had reduced NeuN positive cells (green) in those regions. Representative images from each group are shown. (FIG. 4B)

Dantrolene treated 4L;C* mice had significantly more NeuN positive cells than untreated 4L;C* in each region. In the graph, NeuN positive cell counts in each group are shown as a percentage of WT for each brain region. Data were analysed by One-way ANOVA with post-hoc Tukey test (P<0.05), n=4 images/section, 2 sections/mouse, 3 mice/group.

FIGS. 5A-E. Ryr expression in dantrolene treated 4L;C* brain. (FIG. 5A) Immunoblot of Ryr3 in CBE-N2a cells. Ryr3 protein level was lower in CBE-N2a than N2a cells, and increased in dantrolene treated CBE-N2a cells. (FIG. 5B) 4L;C* cerebrum showed significantly reduced Ryr3 protein at 9% of WT level. In dantrolene treated 4L;C* cerebrum, Ryr3 protein level was significantly increased compared to untreated 4L;C*. 4L;C* panel was spliced to make panel layout consistent with other graphs. A dotted line shows splice area. (FIG. 5C) Immunofluorescence staining of Ryr3.4L;C*midbrain and brain stem showed reduced Ryr3 (green) signal at 49% or 34% of WT level, respectively. In dantrolene treated 4L;C* brain, Ryr3 signal was increased to 94% in midbrain and 79% in brain stem of WT level. DAPI (blue) stained cell nuclei. Scale bar is 20 1.un for all the images. (FIG. 5D and FIG. 5E) CAMK IV and calmodulin (CAM). 4L;C* cerebrum showed decreased level of CAMK IV (FIG. 5D) and increased level of CAM (FIG. 5E) compared to WT. Dantrolene treatment normalized expression of CAMK IV and CAM to nearly WT level One-way ANOVA with post-hoc Tukey test (P<0.05), n=2-3 mice, 2-4 replicates of the experiment FIG. 6. Scheme for generating nGD cell model. A) N2a cells were differentiated in the presence of retinoic acid (RA) and cAMP. The differentiated N2a cells were treated with CBE, a Gcase inhibitor, to generate nGD cells. B) Undifferentiated N2a Cells were stained positive with anti-nestin antibody (green). The differentiated CBE-N2a cells were positive for Map2 (red) a mature neuron marker. Scale bar is same for all images.

Figure 7:
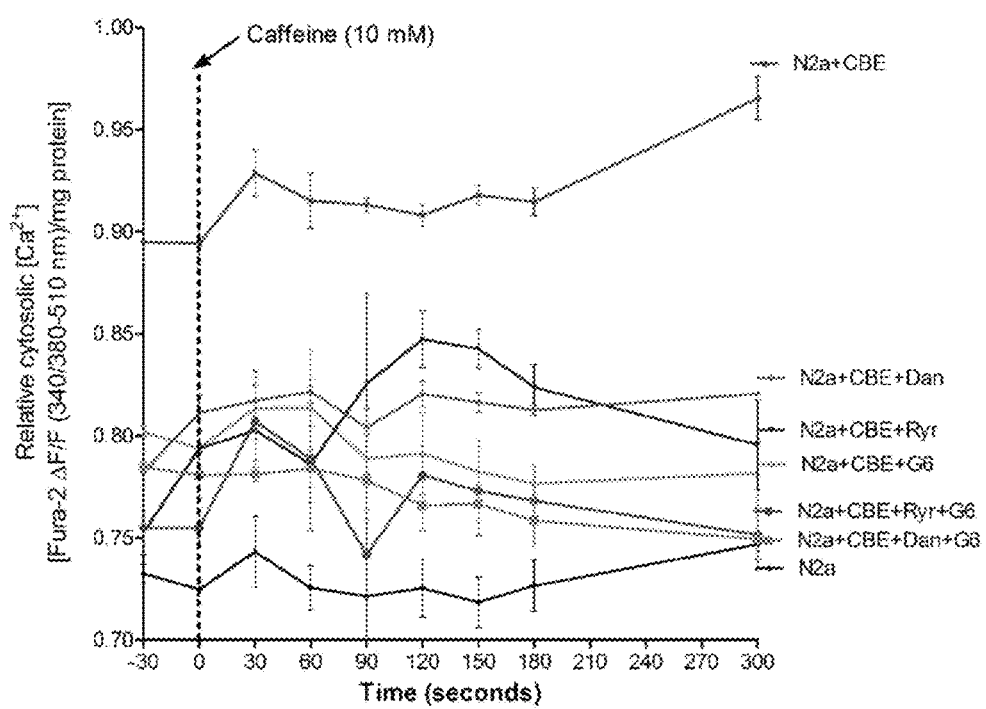

FIG. 7. Recording of cytosolic calcium levels. Differentiated N2a cells were treated with CBE (2 mM) for 5 days. CBE-N2a cells were further incubated for 5 days with ryanodine (Ryan, 10 uM), dantrolene (Dan, 12. uM) or G6 (0.8 uM), or combinations of Dan/G6 or Ryan/G6. Cytosolic calcium levels were measured using Fura-2 as a reporter. Baseline calcium levels were measured prior to caffeine addition (−30 seconds). Cytosolic calcium levels at the baseline (0 second) are the following: (N2a/CBE)>(N2a/CBE/G6)>(N2a/CBE/Dan)~(N2a/CBE/Dan/G6)>(N2a/CBE/Ryr/G6)>(N2a/CBE/Ryr)>(N2a). Calcium levels were recorded every 30 seconds for a duration of 300 seconds after addition of caffeine. CBE-N2a cells treated showed reduced cytosolic calcium levels compared to CBE-N2a cells. Relative cytosolic calcium level (Fura-2 $\Delta$F/F (340/380-510 nm)) for each time point were normalized to mg of protein in the cells. A representative recording of three experiments is shown. Each data point repeated 3 times. Mean±SEM was plotted in the graph.

Figure 8:
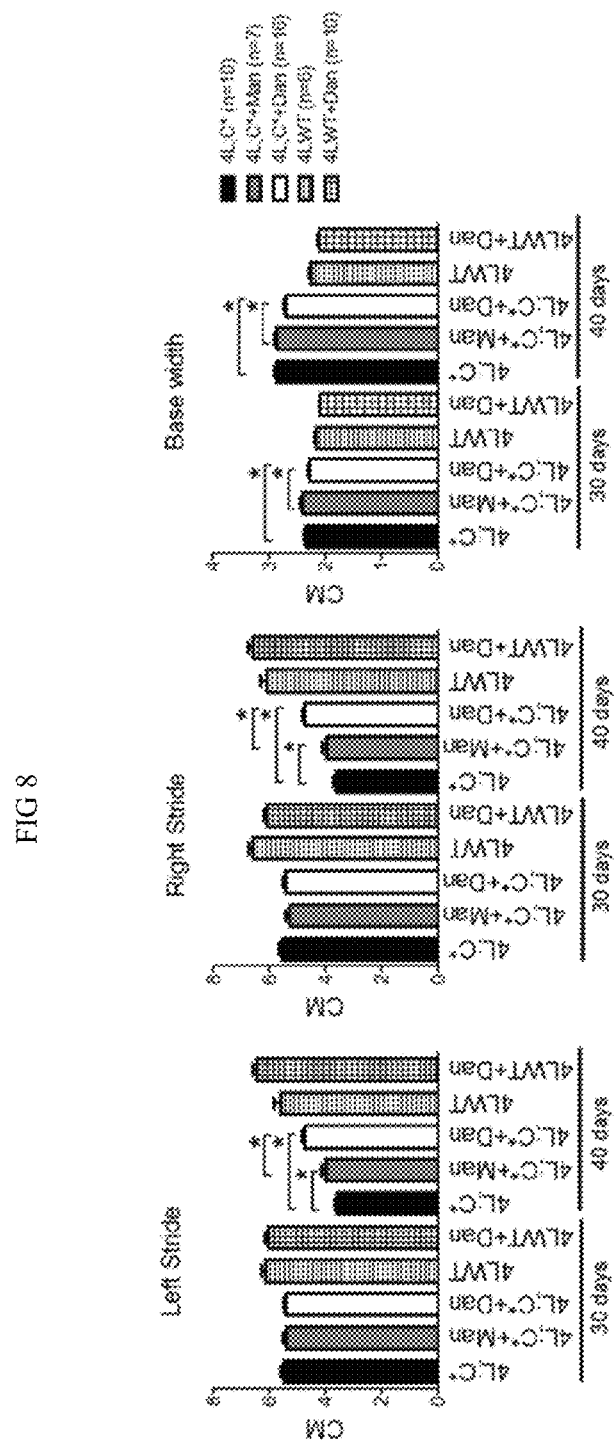

FIG. 8. Gait analysis with mannitol-vehicle group. Left stride (Left panel), right stride (Middle panel), base width (Right panel). The mice were subjected to two to three tests at 30 and 40 days of age. Compared to untreated 4L;C*, mannitol (Man)-4L;C* mice did not show changes in base width. Dantrolene (Dan) treatment significantly reduced base width at both 30 and 40 days of age compared to untreated 4L;C* and Man-4L;C* mice. Both Dan and Man improved left and right strides in 4L;C* mice at 40 days of age, however, Dan-4L;C*mice (10%). Littermate (4L; WT) mice that have no phenotype were used as controls in the analysis. Data were analyzed by Student's t-test.

Figure 9:
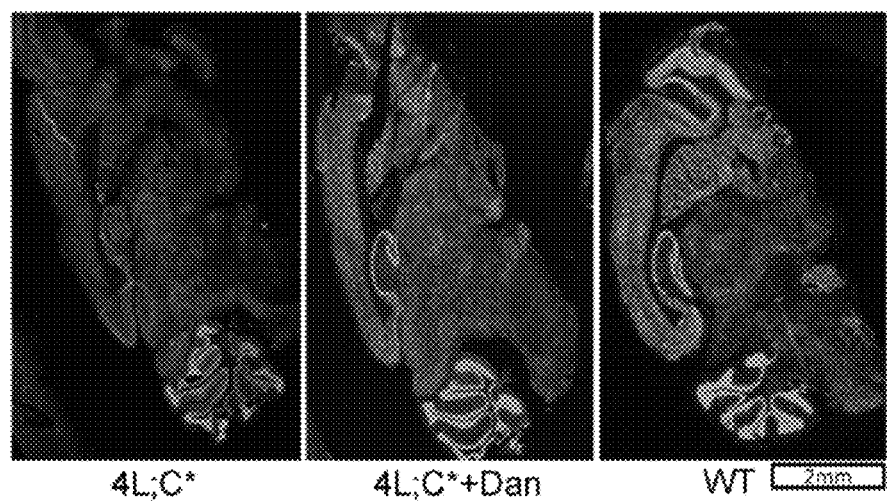
Figure 9:
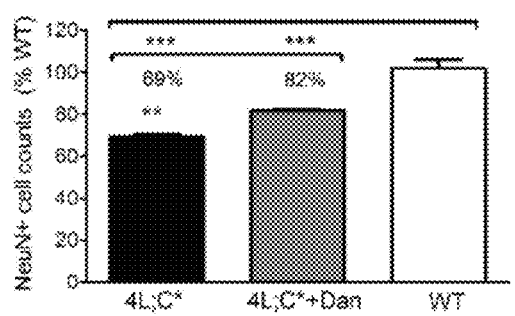

FIG. 9. NeuN positive neurons (green) in brain. (A) WT, dantrolene treated 4L;C* and untreated 4L;c* brains were stained with anti-NeuN antibody. (B) In the graph, NeuN positive cells were quantitated from images of sagittal brain sections by Fiji for Image J and presented as percentage of NeuN positive cells in WT brains. One-way ANOVA with post-hoc Tukey test (p<0.05), (n=6 sections, 2 sections/mouse, 3 mice/group). Scale bar is same for all images.

Figure 10:
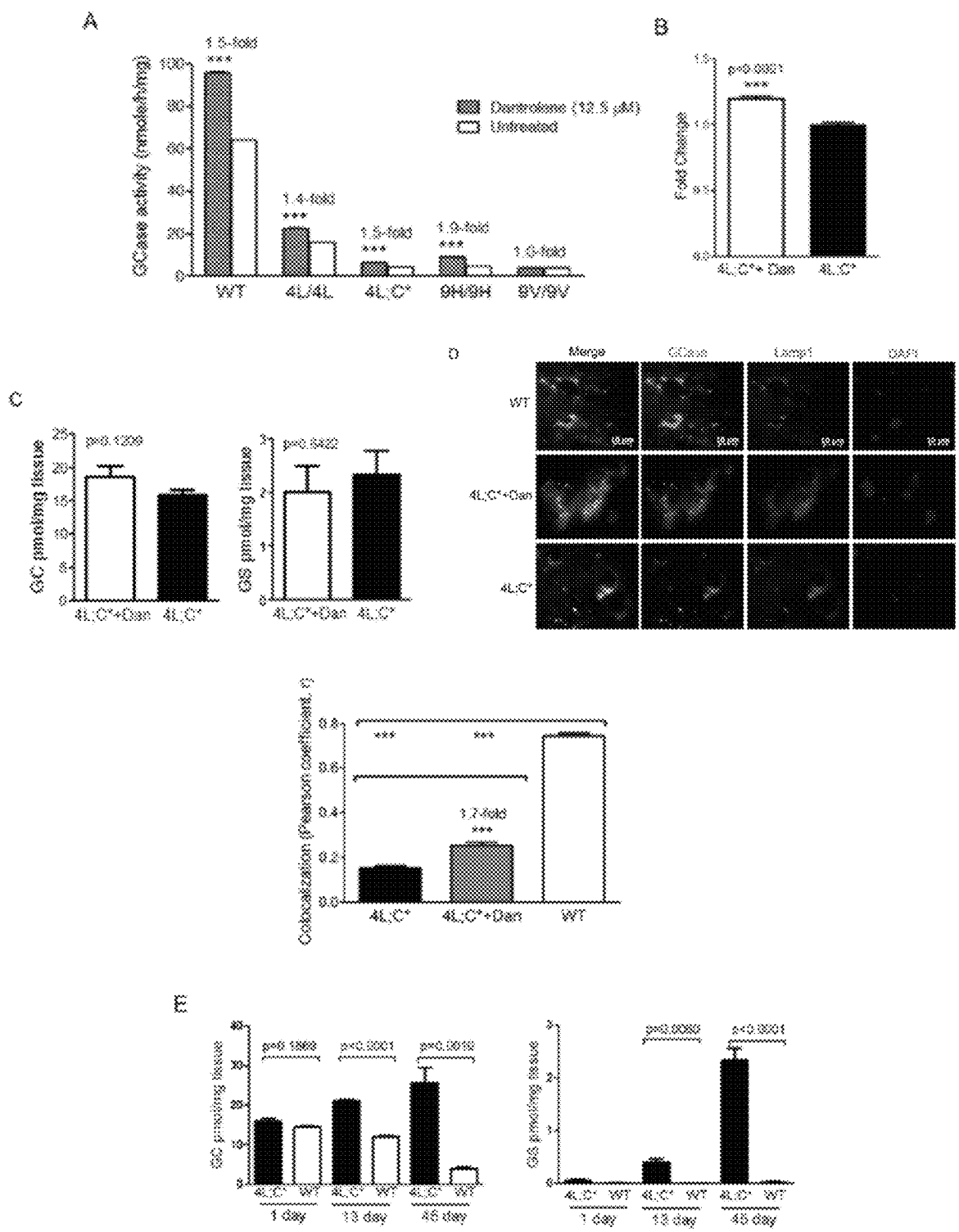

FIG. 10. (A) Increased GCase activity in dantrolene treated fibroblasts. The cells were treated with 12.5 uM dantrolene for 5 days. Dantrolene treatment significantly increased GCase activity in WT, 4L/4L, 4L;C* and 9H/9H fibroblasts, but did not affect GCase in 9V/9V fibroblasts. Student's t-test (n=3 cell lysate samples/genotype, each sample assayed in triplicates). (B) In dantrolene treated mice, brain GCase activity was significantly increased compared to untreated mice at 44 days of age. Student's t-test (n=6 mice/group). (C) Glucosylceramide (GC) concentration was decreased in dantrolene treated 4L;C* brain, but did not reach significance, compared to the untreated 4L;C*. Glucosylsphingosine (GS) concentrations in the dantrolene treated 4L;C* brains were not significantly different from that in the untreated 4L;C* brain. Student's t-test (n=6 mice/group). (D) Co-staining of GCase (green) and Lamp1 (red). A bar graph is plotted at Y-axis of Pearson Correlation Coefficient (PCC, r) calculated from the fluorescence signals of captured images (n=8-13 cells/group) showing the degrees of GCase co-localization with lysosomal marker Lamp 1. PCC was increased 1.7-fold in dantrolene treated 4L;C* compared to untreated 4L;C* brain. One representative image per group is shown. One-way ANOVA with post-hoc Tukey test (p<0.05). Scale bar is same for all images. (E). GC (left panel) and GS (right panel) levels in 4L;C* brain with age. Student's t-test (n=2-10 mice per age group).

DETAILED DESCRIPTION OF THE INVENTION

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

The term "therapeutically effective amount," as used herein, refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt," as used herein, refers to a formulation of a compound that does not cause significant irritation to an organism to which it is administered and does not abrogate the biological activity and properties of the compounds described herein.

The terms "composition" or "pharmaceutical composition," as used herein, refers to a mixture of at least one compound, such as the compounds of Formula (I) provided herein, with at least one and optionally more than one other pharmaceutically acceptable chemical components, such as carriers, stabilizers, diluents, dispersing agents, suspending agents, thickening agents, and/or excipients.

The term "carrier" applied to pharmaceutical compositions of the disclosure refers to a diluent, excipient, or vehicle with which an active compound (e.g., dextromethorphan) is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like. Suitable pharmaceutical carriers are described in "Remington's Pharmaceutical Sciences" by E. W. Martin, 18th Edition.

Disclosed are new treatment strategies for the management of Gaucher disease, which may be similarly applied to treatment of other neurodegenerative disorders such as Parkinson's disease. The disclosed approaches include targeting the disease pathway, balancing glycosphingolipid substrate production and/or degradation, and restoring enzyme folding and trafficking to the lysosome by chaperones.

Gaucher Disease

Gaucher Disease is an autosomal recessively inherited lysosomal storage disease (LSD), caused by mutations on the GBA1 locus. First reported by Dr. Philippe Gaucher in 1882, the primary biochemical defect is enzymatic deficiency of lysosomal acid-β-glucosidase, and is the most common lysosomal storage disease. 90% of LSDs are neuronopathic.

Gaucher disease is caused by mutations in GBA1 that encodes lysosomal acid 11-glucosidase (GCase) that has glucosylceramide (GC) and its un-acylated form, glucosylsphingosine (GS) as substrates (1-3). Gaucher disease is a common lysosomal storage disease with a frequency of 1/57,000 live births (1). Based on neuronopathic involvement, Gaucher disease is classified as type 1 (non-neuronopathic variant) and types 2 and 3 (neuronopathic variants) (1). Type 2 patients present with acute neurological signs and pathology within the first 3 to 6 months of life and with death before 2 years of age (1,4). Type 3 patients exhibit sub-acute neurological signs with a later onset and survival into the 2nd to 4th decade (1,5,6). Two therapeutic strategies have shown clinical efficacy in treating non-neuronopathic Type 1 Gaucher disease and include: 1) enzyme replacement therapy (ERT) and 2) substrate reduction therapy (SRT). However, the enzyme in ERT cannot cross the blood brain bather and the FDA approved SRT compounds, miglustat and eliglustat, do not show effective central nervous system (CNS) rescue (7-9). Thus, nGDs are not amenable to current ERT and SRT. More recently, pharmaceutical chaperones and newly developed small molecule substrate reduction agents have been shown to penetrate into the brain. However, these have limited efficacy in slowing disease progression and they do not alter the disease course or prevent death in animal models (10-15). New therapeutic approaches are needed to protect neuronal function as a crucial goal for nGD intervention as has been a recent focus to manage the CNS disease progression.

Accumulated substrates due to defective GCase function cause pathology in the CNS of Gaucher disease. Studies from human patients, animal models and cell models show involvement of multiple pathological pathways in nGD pathogenesis including, inflammation, mitochondrial dysfunction, disrupted calcium homeostasis, altered autophagy/protease function and necrosis (16-25). Disrupted calcium homeostasis, in particular, is a major pathological factor contributing to many neurodegenerative diseases and may lead to neurological deterioration in GD (18,19,25). Dantrolene is an antagonist of ryanodine receptors (Ryrs) and clinically used for the treatment of malignant hyperthermia and neuroleptic malignant syndrome (26). Ryrs are a class of intracellular calcium channels, expressed in muscles, neurons and other cell types that mediate the release of calcium ions from intracellular organelles, sarcoplasmic reticulum and endoplasmic reticulum (ER). These are essential to a variety of signalling pathways (27). The unique mechanism of dantrolene in blocking intracellular calcium release through Ryrs makes it an attractive potential approach to prevent neuronal dysfunction. Indeed, Applicant has discovered that potential clinical utility for nGD may be possible in view of findings that modulating calcium with dantrolene improves neuronal function in several neurodegenerative diseases including Huntington disease, Alzheimer diseases and kinate-injury model (28-32).

There are three types of Gaucher Disease, as shown in Table 1.

TABLE 1

Types of Gaucher Disease

| Type 1 | Type 2 | Type 3 |
|---|---|---|
| Non-neuronopathic | Acute neuronopathic | Sub-acute neuronopathic |
| Hepatosplenomegaly Bone Disease | Neurodegeneration | Neurodegeneration Visceral involvement |
| 6-80+ years | <2 years | 10-40 years |
| 1/40,000 | 1/100,000 | 1/100,000 |
| Ashkenazi Jews 1/850 | | |

95% are Type 1, 1% are Type 2, and 5% are Type 3. Approximately 400 patients were reported to the International Collaborative Gaucher Registry (2015). Types 2 and 3 are neuronopathic.

Symptoms of neuronopathic Gaucher (nGD) disease include ataxia, dementia, seizures (progressive myoclonic), progressive spasticity, abnormal brainstem auditory evoked potentials; cognitive impairment and pathologic reflexes, dysphagia or apnea. Histologically, neuronal loss, lipid laden macrophages in periadventitial region, gliosis and microglial proliferation are observed. Biochemically, increased levels of glucosylceramide and glucosylsphingosine in the brain are observed. GBA1 mutations confer a 20-30-fold increased risk for development of Parkinson's disease (PD). Approximately 7-10% of PD patients have a GBA1 mutation, and GBA1 is listed as one of the target genes for disease modifying strategies for Parkinson's disease by The Michael J. Fox Foundation. The proposed mechanism of Gaucher disease linked Parkinson's disease. See Mazulli et al., Cell V146:37-52, 8 Jul. 2011.

Currently, clinical therapies for Gaucher disease include Enzyme replacement therapy (ERT) and Substrate reduction therapy (SRT). ERT treatments include Cerezyme (imiglucerase) (Genzyme), VPRIV (velaglucerase alfa) (Shire), and ELELYSO (taliglucerase alfa) (Pfizer). SRT treatments include Cerdelga (eliglustat) (Genzyme), and Zavesca (miglustat) (Actelion). ERT increases Acid-beta-glucosidase (GCase), whereas SRT decreases glucosylceramide synthase (GCS).

Applicant has discovered a novel treatment method for Gaucher disease, particularly type II and III neuronopathic Gaucher disease (nGD).

In one aspect, the instant disclosure provides a method of treating an individual having Gaucher disease (nGD), in particular type II or type III, comprising the step of administering an effective amount of a ryanodine receptor inhibitor or a pharmaceutically acceptable salt thereof. In one aspect, the ryanodine receptor antagonist can be any ryanodine receptor antagonist known in the art.

In one aspect, the ryanodine receptor inhibitor may be selected from dantrolene, JTV-519, Flecainide-d3, Flecainide, 4-(2-Aminopropyl)-3,5-dichloro-N,N-dimethylaniline (FLA 365), DHBP (1,1'-diheptyl-4,4'-bipyridium), Ruthenium red (R2751), Ryanodine, or a combination thereof.

JTV-519 is a potent inhibitor or the ryanodine receptor 2 (RYR2) blocker. RYR2 is a cardiac calcium channel that regulates calcium levels in the sarcoplasmic reticulum. JTV-519 stabilizes RYR2 in the closed state. (See, e.g., Science. 2004 Apr. 9; 304(5668):292-6. Protection from cardiac arrhythmia through ryanodine receptor-stabilizing protein calstabin2. Wehrens XH1, Lehnart S E, Reiken S R, Deng S X, Vest J A, Cervantes D, Coromilas J, Landry D W, Marks A R.)

Flecainide-d3 is a deuterated version of the antiarrythmic, Flecainide. (See, e.g., Mol Pharmacol. 2014 December; 86(6):696-706. doi: 10.1124/mol.114.094623. Epub 2014 Oct. 1. Multiple modes of ryanodine receptor 2 inhibition by flecainide. Mehra D1, Imtiaz MS1, van Helden DF1, Knollmann BC1, layer DR2.)

Flecainide is an antiarrythmic RyR-2 inhibitor (See, e.g., Mol Pharmacol. 2014 December; 86(6):696-706. doi: 10.1124/mol.114.094623. Epub 2014 Oct. 1. Multiple modes of ryanodine receptor 2 inhibition by flecainide. Mehra D1, Imtiaz MS1, van Helden DF1, Knollmann BC1, layer DR2.)

4-(2-Aminopropyl)-3,5-dichloro-N,N-dimethylaniline (FLA 365)—See, e.g., Inhibition of Ryanodine Receptors by 4-(2-Aminopropyl)-3,5-dichloro-N,N-dimethylaniline (FLA 365) in Canine Pulmonary Arterial Smooth Muscle Cells, Olga Ostrovskaya, Ravi Goyal, Noah Osman, Claire E. McAllister, Isaac N. Pessah, Joseph R. Hume and Sean M. Wilson, Journal of Pharmacology and Experimental Therapeutics October 2007, 323 (1) 381-390; DOI: https://doi.org/10.1124/jpet.107.122119.

DHBP (1,1'-diheptyl-4,4'-bipyridium)—See, e.g., J Neurosci Res. 2007 Aug. 1; 85(10):2207-15. Functional ryanodine receptors are expressed by human microglia and THP-1 cells: Their possible involvement in modulation of neurotoxicity. Klegeris A1, Choi H B, McLarnon J G, McGeer P L Additional ryanodine receptor antagonists include Ruthenium red (µM) (R2751), Ryanodine (>10 µM), Imperatoxin (nM) (I148), and Dantrolene (µM) (D9175), all of which are available from Sigma.

In one aspect, the ryanodine receptor inhibitor may be administered in an amount sufficient to reduce nGD associated autophagy. Reduced autophagy may be determined by reduced LC3-II levels as compared to pre-treatment levels in an individual.

In one aspect, the ryanodine receptor may be administered in an amount sufficient to improve mitochondrial function.

In one aspect, the ryanodine receptor may be administered in an amount sufficient to improve sensory motor function.

In one aspect, the ryanodine receptor may be administered in an amount sufficient to increase or maintain Ryrs expression.

Further disclosed are methods of improving survival in an individual having nGD Type II or Type III. The method may comprise the step of administering an effective amount of a ryanodine receptor inhibitor.

Further disclosed is an article of manufacture. The article of manufacture may comprise a container comprising a label; and a composition comprising a ryanodine receptor inhibitor or a pharmaceutically acceptable salt thereof and a pharmaceutically acceptable carrier, wherein the label indicates that the composition for the treatment of an individual having nGD Type II or Type III. The article of manufacture may further comprise a means for delivery of said composition to an individual in need thereof Dosage As will be apparent to those skilled in the art, dosages outside of these disclosed ranges may be administered in some cases. Further, it is noted that the ordinary skilled clinician or treating physician will know how and when to interrupt, adjust, or terminate therapy in consideration of individual patient response.

In one aspect, the dosage of an agent disclosed herein, based on weight of the active compound, administered to an individual in need thereof may be about 0.25 mg/kg, 0.5 mg/kg, 0.1 mg/kg, 1 mg/kg, 2 mg/kg, 3 mg/kg, 4 mg/kg, 5 mg/kg, 6 mg/kg, or more of a subject's body weight. In another embodiment, the dosage may be a unit dose of about 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In one aspect, an agent disclosed herein may be present in an amount of from about 0.5% to about 95%, or from about 1% to about 90%, or from about 2% to about 85%, or from about 3% to about 80%, or from about 4%, about 75%, or from about 5% to about 70%, or from about 6%, about 65%, or from about 7% to about 60%, or from about 8% to about 55%, or from about 9% to about 50%, or from about 10% to about 40%, by weight of the composition.

The compositions may be administered in oral dosage forms such as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular forms all utilizing dosage forms well known to those of ordinary skill in the pharmaceutical arts. The compositions may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen.

A dosage regimen will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect. The effective amount of a drug required to prevent, counter, or arrest progression of a symptom or effect of Gaucher disease can be readily determined by an ordinarily skilled physician Compositions may include suitable dosage forms for oral, parenteral (including subcutaneous, intramuscular, intradermal and intravenous), transdermal, sublingual, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. Oral preparations include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. For topical or nasal administration, penetrants or permeation agents that are appropriate to the particular barrier to be permeated are used in the formulation. Such penetrants are generally known in the art. The pharmaceutical compositions are prepared by conventional techniques appropriate to the desired preparation containing appropriate amounts of the active ingredient, that is, one or more of the disclosed active agents or a pharmaceutically acceptable salt thereof according to the invention.

The dosage of an agent disclosed herein used to achieve a therapeutic effect will depend not only on such factors as the age, weight and sex of the patient and mode of administration, but also on the degree of inhibition desired and the potency of an agent disclosed herein for the particular disorder or disease concerned. It is also contemplated that the treatment and dosage of an agent disclosed herein may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

Kits

Kits are also provided. In one aspect, a kit may comprise or consist essentially of agents or compositions described herein. The kit may be a package that houses a container which may contain a composition comprising an oxime or pharmaceutically acceptable salt thereof as disclosed herein, and also houses instructions for administering the agent or composition to a subject. In one aspect, a pharmaceutical pack or kit is provided comprising one or more containers filled with one or more composition as disclosed herein. Associated with such container(s) can be various written materials such as instructions for use, or a notice in the form prescribed by a governmental agency regulating the manufacture, use or sale of pharmaceuticals or biological products, which notice reflects approval by the agency of manufacture, use, or sale for human administration.

As there may be advantages to mixing a component of a composition described herein and a pharmaceutically acceptable carrier, excipient or vehicle near the time of use, kits in which components of the compositions are packaged separately are disclosed. For example, the kit can contain an active ingredient in a powdered or other dry form in, for example, a sterile vial or ampule and, in a separate container within the kit, a carrier, excipient, or vehicle, or a component of a carrier, excipient, or vehicle (in liquid or dry form). In one aspect, the kit can contain a component in a dry form, typically as a powder, often in a lyophilized form in, for example, a sterile vial or ampule and, in a separate container within the kit, a carrier, excipient, or vehicle, or a component of a carrier, excipient, or vehicle. Alternatively, the kit may contain a component in the form of a concentrated solution that is diluted prior to administration. Any of the components described herein, any of the carriers, excipients or vehicles described herein, and any combination of components and carriers, excipients or vehicles can be included in a kit.

Optionally, a kit may also contain instructions for preparation or use (e.g., written instructions printed on the outer container or on a leaflet placed therein) and one or more devices to aid the preparation of the solution and/or its administration to a patient (e.g., one or a plurality of syringes, needles, filters, tape, tubing (e.g., tubing to facilitate intravenous administration) alcohol swabs and/or the Band-Aid® applicator). Compositions which are more concentrated than those administered to a subject can be prepared. Accordingly, such compositions can be included in the kits with, optionally, suitable materials (e.g., water, saline, or other physiologically acceptable solutions) for dilution. Instructions included with the kit can include, where appropriate, instructions for dilution.

In other embodiments, the kits can include pre-mixed compositions and instructions for solubilizing any precipitate that may have formed during shipping or storage. Kits containing solutions of Compound I, or a pharmaceutically acceptable salt thereof, and one or more carriers, excipients or vehicles may also contain any of the materials mentioned above (e.g., any device to aid in preparing the composition for administration or in the administration per se). The instructions in these kits may describe suitable indications (e.g., a description of patients amenable to treatment) and instructions for administering the solution to a patient.

EXAMPLES

Neuronopathic Gaucher disease (nGD) manifests as severe neurological symptoms in patients with no effective treatment available. Ryanodine receptors (Ryrs) are a family of calcium release channels on intracellular stores. The following data was used to determine if Ryrs are potential targets for nGD treatment. A nGD cell model (CBE-N2a) was created by inhibiting acid/3-glucosidase (GCase) in N2a cells with conduritol B epoxide (CBE). Enhanced cytosolic calcium in CBE-N2a cells was blocked by either ryanodine or dantrolene, antagonists of Ryrs and by Genz-161, a glucosylceramide synthase inhibitor, suggesting substrate-mediated ER-calcium efflux occurs through ryanodine receptors. In the brain of a nGD (4L;C) mouse model, expression of Ryrs was normal at 13 days of age, but significantly decreased below the wild type level in end-stage 4L;C* brains at 40 days. Treatment with dantrolene in 4L;C* mice starting at postnatal day 5 delayed neurological pathology and prolonged survival. Compared to untreated 4L;C* mice, dantrolene treatment significantly improved gait, reduced LC3-II levels, improved mitochondrial ATP production and reduced inflammation in the brain. Dantrolene treatment partially normalized Ryr expression and its potential regulators, CAMK IV and calmodulin. Furthermore, dantrolene treatment increased residual mutant GCase activity in 4L;C* brains. These data demonstrate that modulating Ryrs has neuroprotective effects in nGD through mechanisms that protect the mitochondria, autophagy, Ryr expression and enhance GCase activity. This study suggests that calcium signalling stabilization, e.g. with dantrolene, could be a potential disease modifying therapy for nGD.

Here, nGD cell (CBE-N2a) and mouse (4L;C*) models were used to determine the biochemical, histological, and behavioural effects of dantrolene in nGD. The 4L;C* model is a viable analog of human nGD that develops progressive accumulation of substrates and CNS pathology and symptoms (4,18,33,34). 4L;C* mice have been used to investigate pathological mechanisms and test potential therapeutics for nGD (14,18,35). The present study shows dantrolene treatment improves mitochondrial function and protects Ryrs expression in nGD cell and mouse models. Furthermore, dantrolene treatment improved gait, reduced inflammation and prolonged survival in 4L;C* mice, establishing therapeutic potential for dantrolene in nGD.

Results

Ryrs Expression in Brain of the nGD Mouse Model

Figure 1A:
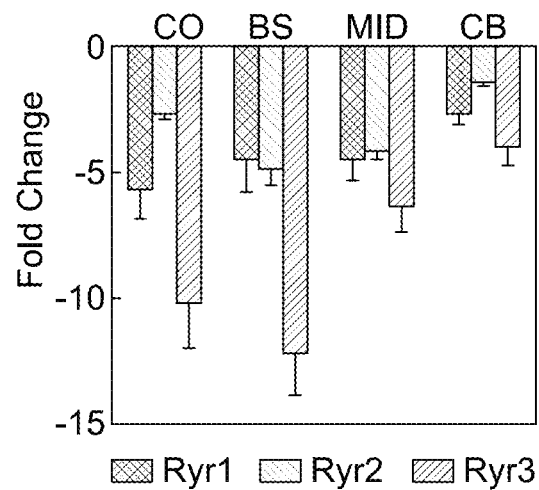
FIGS. 1A-1D. Ryrs expression in 4L;C* mouse brains.
Figure 1B:
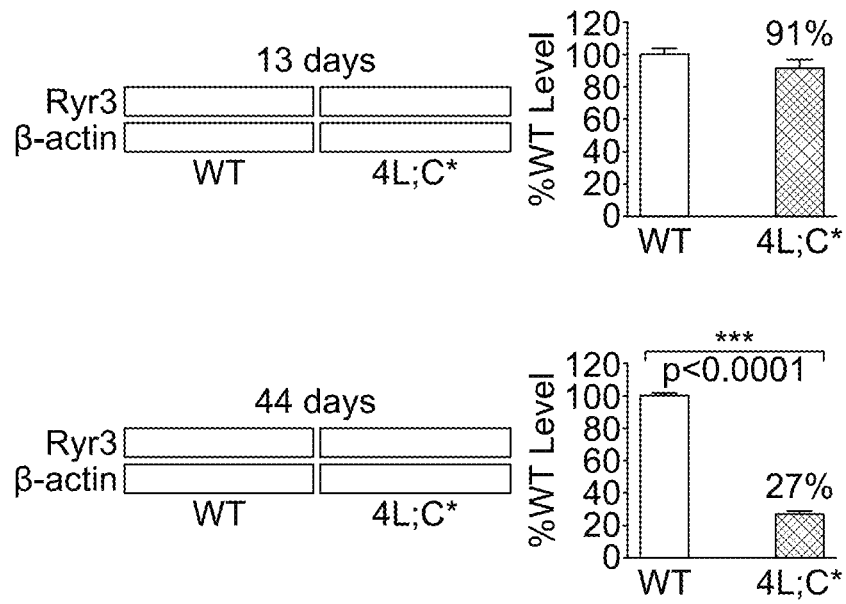
Figure 1C:
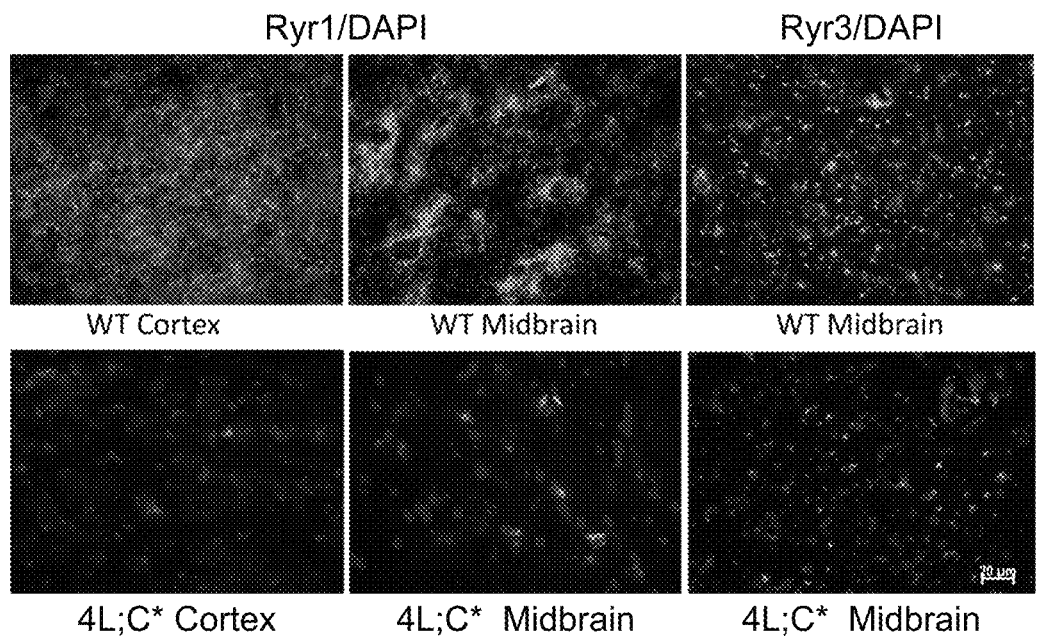
Figure 1D:
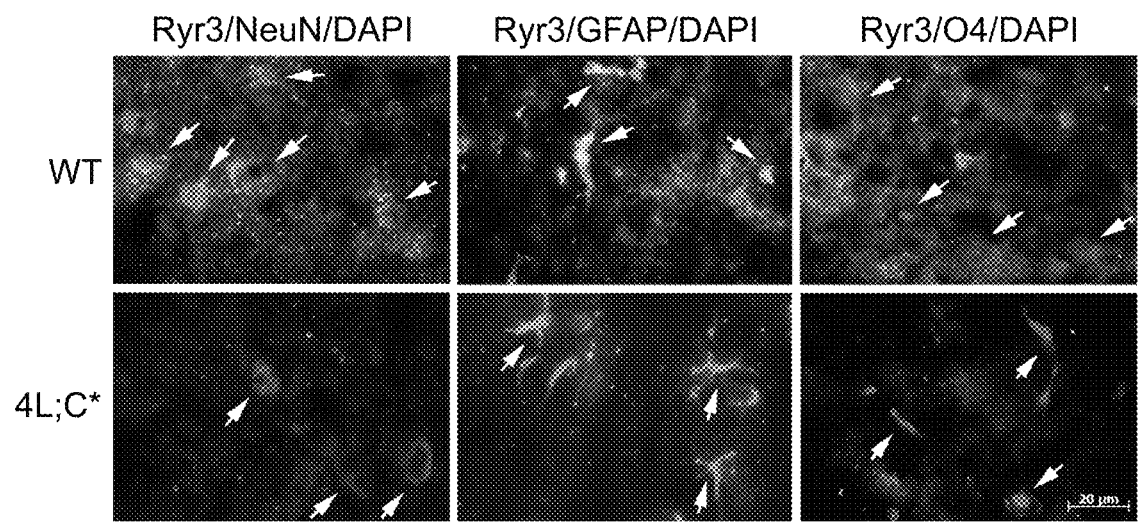

The nGD mouse model (4L;C*) has the homozygous Gba1 mutation V394L/V394L and a lack of saposin C (33). The 4L;C* mice have substrate (GC and GS) accumulation in the brain that increases with age and is associated with progressive gait impairment, brain pathology, and survival limited to approximately 45 days (14,18,33). Transcriptome analysis by RNAseq of cortex, brain stem, midbrain and cerebellum of 4L;C* mice brains showed a reduction of Ryr1, Ryr2 and Ryr3 mRNAs at 44 days of age (FIG. 1A) (18). Although all three Ryrs are expressed in the brain, Ryr2 is predominantly seen in cardiac muscle (27,36). Levels of Ryrs protein in neuronal cells and mouse brains were determined for Ryr3 or Ryr1 Immunoblot analysis showed Ryr3 protein in 4L;C* brains was maintained at wild-type (WT) levels at 13 days of age, but was significantly reduced to 27% of WT level at 44 days of age, the end-stage of the disease (FIG. 1B). Immunofluorescence staining with anti-Ryr1 and anti-Ryr3 antibodies showed that Ryrs signal at 44-days in 4L;C* cortex and midbrain was reduced below WT levels (FIG. 1C). Neural cells expressing Ryrs were characterized by co-staining of anti-Ryr3 antibody with either anti-NeuN (neuron), anti-GFAP (astro-cyte), or anti-04 (oligodendrocyte) antibodies, respectively. The results showed that Ryr3 was expressed in neurons, astrocytes and oligodendrocytes (FIG. 1D). 4L;C* brains had reduced Ryr3 levels in all three cell types (FIG. 1D). These data demonstrate a reduction of Ryrs expression in 4L;C* brains at the disease end-stage implicating Ryrs in nGD pathogenesis.

Dantrolene Blocks Substrate-Mediated Calcium Efflux from Ryrs in nGD Cells

Figure 2:
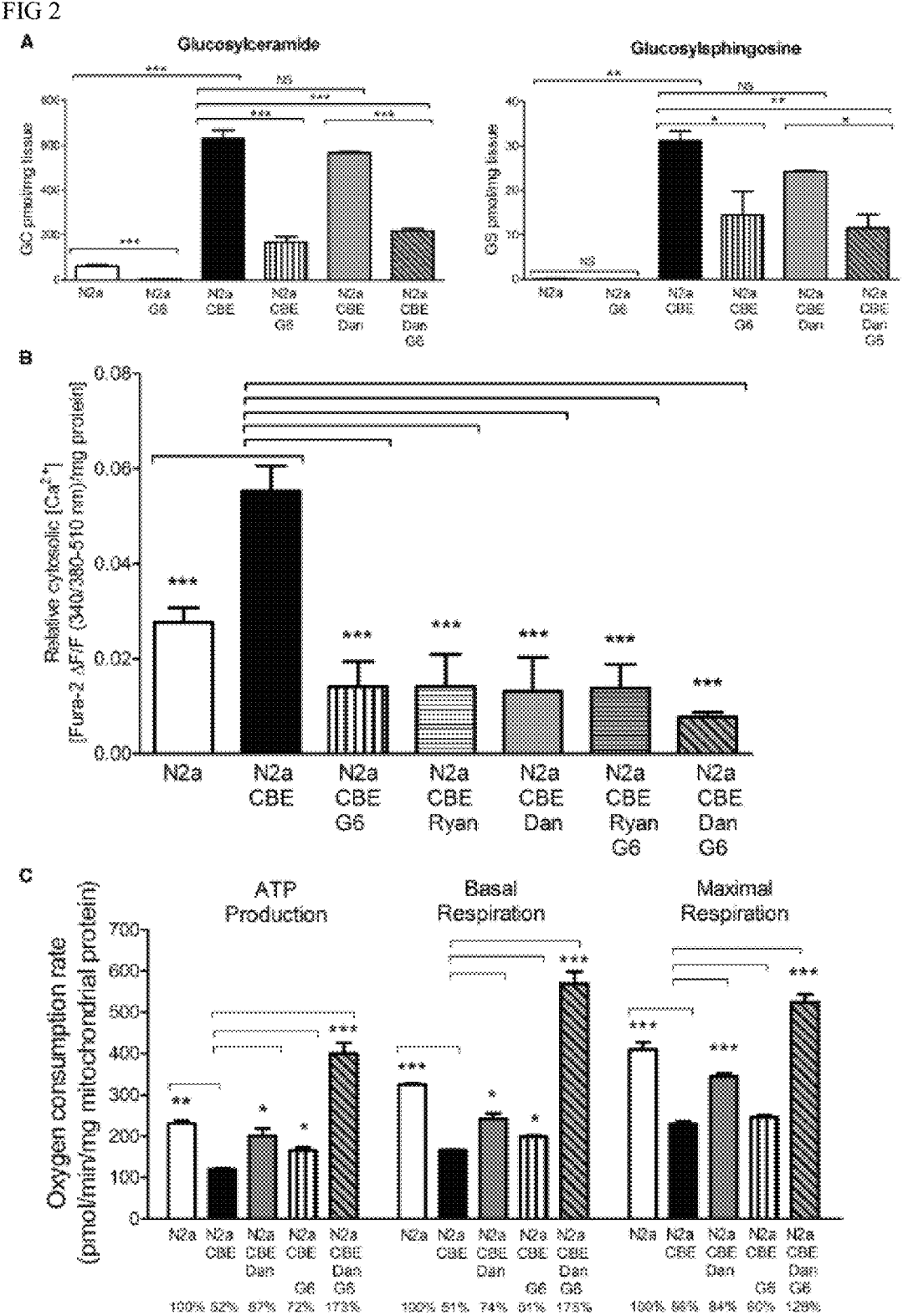
FIG. 2. Substrates, calcium levels and mitochondrial function in nGD (CBE-N2a) cells. (A) Substrates levels. GC and GS concentration was significantly increased in CBE-N2a cells compared to N2a cells. Treatment with G6 led to a significant reduction of GC and GS in N2a and CBE-N2a cells, respectively. Dantrolene alone did not significantly affect GC and GS levels in CBE-N2a cells. CBE-N2a cells treated with both G6 and dantrolene showed similar level of GC and GS reduction to G6 alone. (B) Cytosolic calcium levels. Differentiated N2a cells were treated with CBE (2 mM) for 5 days. CBE-N2a cells were further incubated for 5 days with ryanodine (Ryan, 10 dantrolene (Dan, 12.5 AM) or G6 (0.8 I.LM), or combinations of Dan/G6 or Ryan/G6. Cytosolic calcium level was measured using Fura-2 as reporter after adding caffeine. Relative cytosolic calcium level [Fura-2 AF/F (340/380-510 nm)] normalized to mg protein in cells shows the magnitude of cytosolic calcium above baseline (see method). CBE-N2a cells had significant higher cytosolic calcium levels than N2a cells. Ryanodine, dantrolene, and G6 significantly reduced cytosolic calcium levels in CBE-N2a cells. Combinations of Dan/G6 or Ryan/G6 in CBE-N2a cells also caused significant decrease in cytosolic calcium levels. (C) Mitochondrial function in N2a cells. Reduced oxygen consumption rate (OCR, pmol/min/mg mitochondrial protein) parameters (ATP production, basal respiration and maximal respiration) in CBE-N2a cells were reduced compared to N2a cells. Dantrolene or G6 treatment significantly improved OCR in CBE-N2a cells compared to untreated CBE-N2a cells. Relative levels of OCR in treated cells compared to N2a were indicated below the graph. Each data are from 2 to 4 experiments (n=3 cell or cell lysate samples/treatment group, six replicates/sample/experiment) and reported as mean±SEM. One-way ANOVA with post-hoc Tukey test (P<0.05).

GC mediates ER calcium release (25). To determine if Ryrs are involved in substrate-mediated ER calcium release, a new nGD cell model (CBE-N2a) was generated using N2a cells. N2a is a mouse neuroblastoma cell line that can be differentiated into mature neurons by cAMP and retinoic acid (FIG. 6) (37). Differentiated N2a cells were treated with conduritol B epoxide (CBE), an irreversible covalently bound GCase inhibitor. This resulted in significant GC and GS accumulation in CBE-N2a cells, thereby creating an nGD model (FIG. 2A). The effects of Genz-161 (G6), an inhibitor of glucosylceramide synthase to reduce the production of the substrates GC and GS, were evaluated in CBE-N2a cells (14). Treating N2a and CBE-N2a cells with G6 gave GC reductions to 7% and 26% of untreated levels, respectively (FIG. 2A). G6 treated CBE-N2a also had significantly decreased GS (FIG. 2A). Dantrolene is an antagonist of Ryrs and blocks Ryr-mediated ER calcium release (17). Dantrolene alone did not affect GC and GS levels in CBE-N2a cells (FIG. 2A). Co-treatment of G6 and dantrolene of CBE-N2a cells led to a similar degree of GC and GS reduction as G6 alone, indicating a specific effect of G6 on inhibition of substrate accumulation (FIG. 2A). These results demonstrate that G6 inhibits GC production and reduces substrate accumulation in CBE-N2a cells.

Using CBE-N2a cells as an nGD cell model, the effects of dan-trolene, ryanodine and G6 on substrate-mediated ER-calcium release were evaluated (FIG. 2B). After CBE-N2a cells were treated with those agents, baseline calcium levels were recorded prior caffeine addition. CBE-N2a cells have higher calcium levels than in N2a cells without caffeine at baseline (FIG. 7). Caffeine is a stimulant or releaser of calcium from ER stores for monitoring GC/GS-mediated ER-calcium levels and the Ryr response (38,39). After adding caffeine, cytosolic calcium levels were measured every 30 s over the duration of 300 s using Fura-2 (FIG. 7). The magnitude of cytosolic calcium above baseline in the cells with each treatment is shown in FIG. 2B. CBE-N2a cells showed a significant increase in cytosolic calcium levels compared to N2a cells. When CBE-N2a cells were treated with G6, the calcium levels were significantly lower than that in untreated CBE-N2a cells (FIG. 2B), suggesting substrate-mediated calcium release. In dantrolene-treated CBE-N2a cells, calcium levels were significantly reduced compared to untreated CBE-N2a and approached levels observed in control N2a cells (FIG. 2B). Consistent with dantrolene, CBE-N2a cells treated with ryanodine also showed a significant reduction in calcium levels (FIG. 2B). Co-treatment of G6 and dantrolene or G6 and ryanodine also showed a significant decrease in calcium levels. These results demonstrate that substrate-mediated calcium release occurs through Ryrs.

Dantrolene Protects Mitochondrial Function in nGD Cells

To determine if substrate-mediated ER calcium efflux promotes mitochondrial dysfunction, the effects of dantrolene and G6 on mitochondrial function were evaluated in CBE-N2a cells. Treated cells were plated on a Seahorse plate to assay mitochondrial function reported as Oxygen Consumption Rate (OCR) that includes the following parameters: ATP production, basal respiration, and maximal respiration. CBE-N2a cells showed a significant reduction in OCR as evidenced by approximately 50% in all the parameters, including rate of ATP production, basal respiration, and maximal respiration, compared to N2a cells, indicating reduced mitochondrial function in this nGD cell model (FIG. 2C). Dantrolene treatment significantly improved OCR in CBE-N2a cells (FIG. 2C). G6 treatment also resulted in significant increases in OCR in CBE-N2a cells (FIG. 2C). The greatest increase in OCR was achieved when CBE-N2a cells were treated with both dantrolene and G6 (FIG. 2C). These results demonstrate that both reduction of substrate levels by G6 or antagonizing Ryrs by dantrolene have protective effects on mitochondrial function in nGD cells. Combining G6 and dantrolene resulted in more improvement than either dantrolene or G6 alone.

Dantrolene Treatment Mitigates the Neuropathic Phenotype in the nGD Mouse Model

The in vivo efficacy of dantrolene on nGD was evaluated in the 4L;C* mouse model. 4L;C* mice were treated with dantrolene by intraperitoneal (IP) injection at 10 mg/kg on each of three days per week, starting from postnatal day 5. Because dantrolene formulation contains mannitol, two control groups were included in the study: untreated 4L;C* mice and 4L;C* mice injected with mannitol at 30 mg/kg (same level of mannitol in dantrolene formulation) on each of three days per week. Dantrolene treated littermates (4L;WT) were also included as controls. These litter-mates do not show neurological impairments and live beyond 80 days.

Figure 3A:
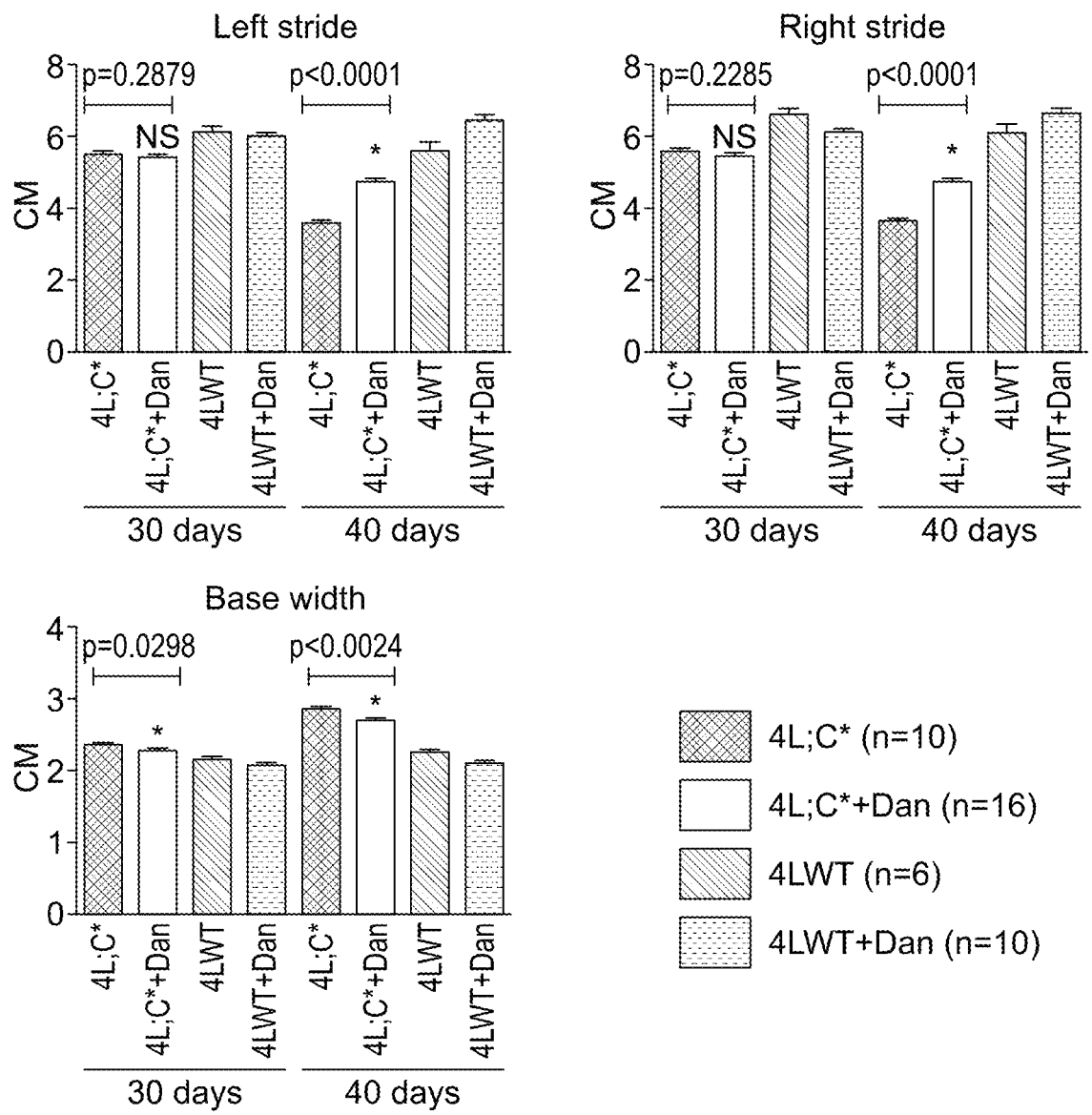
FIGS. 3A-E. Dantrolene treatment in 4L;C* mice.

Gait was measured at 30 and 40 days of age. 4L;C* mice typically develop a duck-like walking with paralysis of the hind limbs (18,33). Untreated 4L;C* mice made significantly shorter strides and had a wider base width at 30 and 40 days of age compared to 4L;WT littermates (FIG. 3A). Dantrolene treatment significantly reduced base stride width at 30 and 40 days of age compared to age-matched untreated 4L;C* mice (FIG. 3A).

Figure 3B:
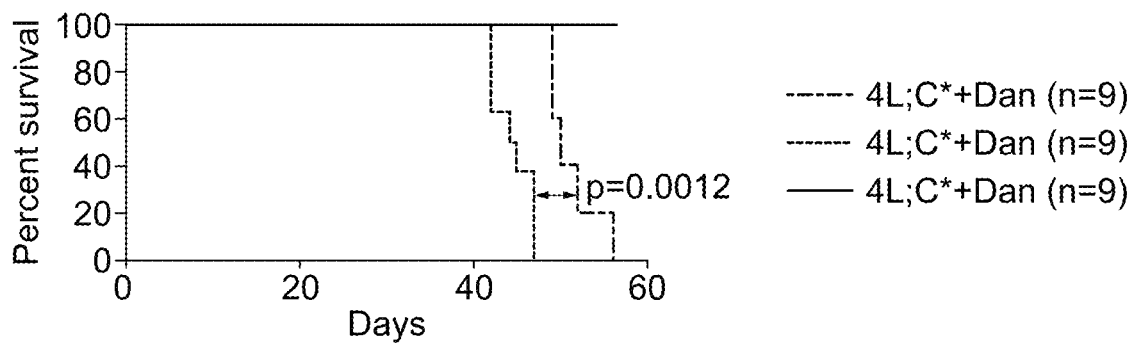

Dantrolene treated 4L;C* mice made significantly longer strides, a 30% increase compared to untreated 4L;C* mice at 40 days of age (FIG. 3A). However, the gait in dantrolene treated 4L;C* mice did begin to deteriorate after 50 days of age (data not shown). The life span of dantrolene treated 4L;C* mice was also significantly extended compared to untreated 4L;C* mice (P=0.0012) as determined by Kaplan-Meier analyses and the Mantel-Cox test (FIG. 3B). The treatment prolonged survival in 4L;C* mice by 12.7% compared to untreated 4L;C* mice (FIG. 3B). To determine if mannitol would affect the phenotype, one group of 4L;C* mice was injected with mannitol and gait and survival were evaluated. Mannitol-4L;C* mice showed no changes on base width, but they had a 10% increase (P<0.05) in stride length compared to untreated 4L;C* mice at 40 days of age. However, this improvement is significantly less than the 30% improvement in dantrolene treated 4L;C* mice (FIG. 8). No differences were observed in life span between untreated and mannitol-treated 4L;C* mice (data not shown), indicating a specific effect of dantrolene on survival. In the following biochemical and histological studies, untreated 4L;C* brains were used as a control for dantrolene treatment effect. Dantrolene treatment did not affect body or organ weights in treated mice. These results demonstrate that dantrolene significantly improved gait, delayed motor function decline, and extended the life span of 4L;C* mice.

Figure 3C:
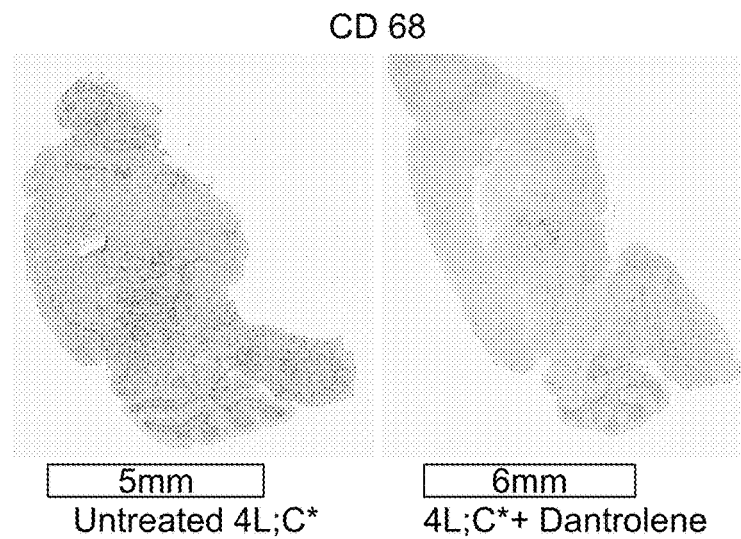

CNS inflammation was determined by staining tissue sections with an anti-CD68 antibody. CD68 is a marker for activated microglia and macrophages. Positive CD68 signals (brown) were detected in most brain regions of untreated 4L;C* mice (FIG. 3C). With dantrolene treatment, the CD68 signal showed a significant decrease of 63% of that in untreated mice, indicating attenuation of CNS inflammation by dantrolene (FIG. 3C).

Figure 3D:
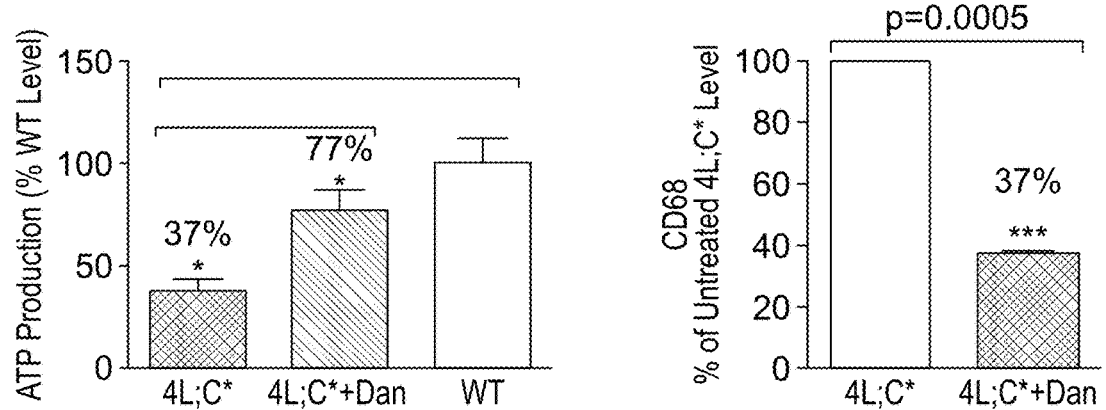

Brain mitochondrial function was determined by Seahorse assay using isolated mitochondria from WT, untreated and dantrolene treated 4L;C* brains at 40 days of age. ATP production rate in 4L;C* brain mitochondria was significantly reduced compared to WT (FIG. 3D). Dantrolene treated 4L;C* mice showed significantly increased mitochondrial ATP production rate in the brain, 77% of WT level compared to 37% in the untreated 4L;C* brain (FIG. 3D) indicating a protection of mitochondrial function in nGD by dantrolene.

Figure 3E:
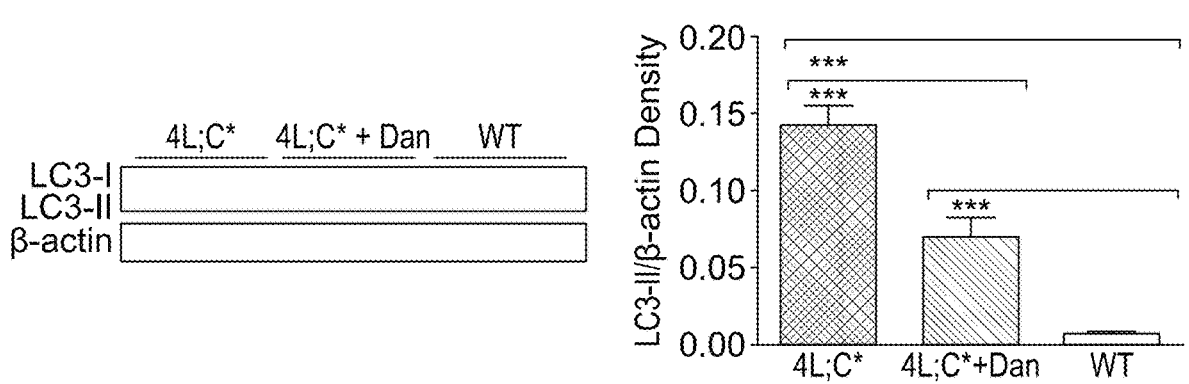

Altered autophagy is also evident in nGD and 4L;C* mouse brains (20,33,34). LC3-II is a marker for autophagy activity and was evaluated in dantrolene treated 4L;C* brains compared to untreated 4L;C* and WT brains to determine the effect of the treatment on autophagy function. LC3-II is a membrane bound form of LC3. Elevated LC3-II levels indicate altered autophagy. By immunoblot analysis, LC3-II was undetectable in WT brain. Increased LC3-II levels were observed in untreated 4L;C* brains whereas dantrolene treated 4L;C* brains had significantly reduced LC3-II levels at 50% of untreated level, but still more than WT level (FIG. 3E). This result indicated that dantrolene treatment partially prevented alterations in autophagy in 4L;C* brains.

Figure 4A:
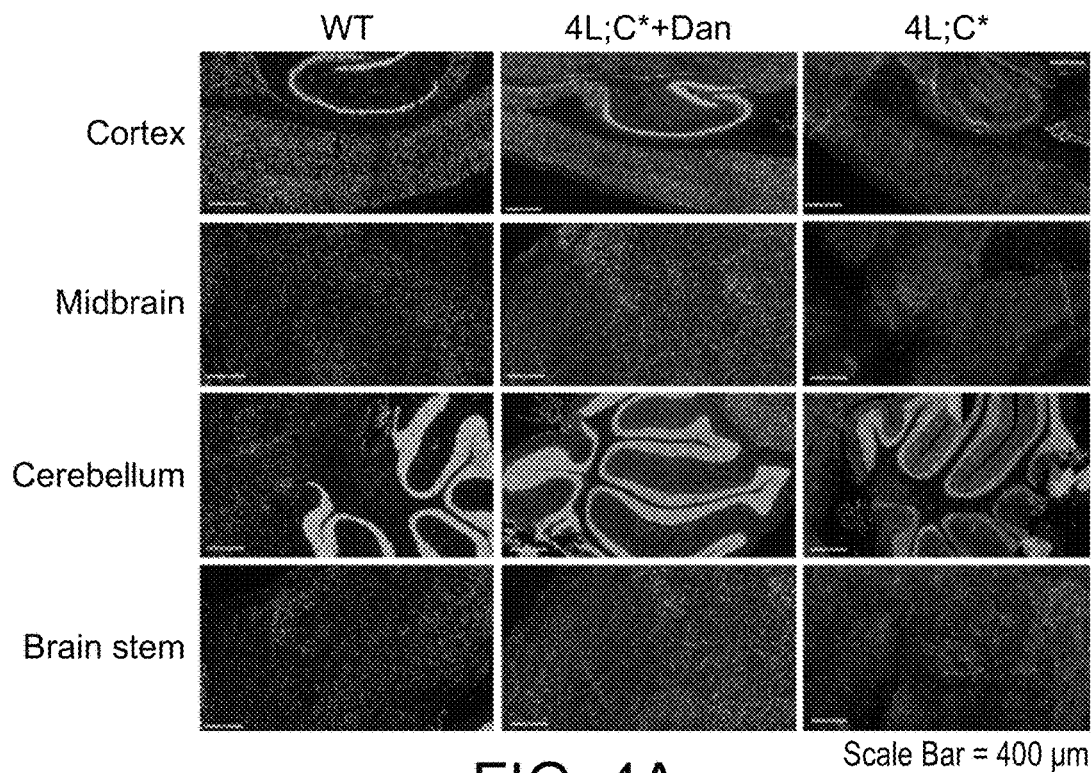
FIGS. 4A-B. NeuN positive neurons in brain regions. WT, dantrolene (Dan) treated 4L;C* and untreated 4L;C* brain sagittal sections from 44 day old mice were stained with anti-NeuN antibody.
Figure 4B:
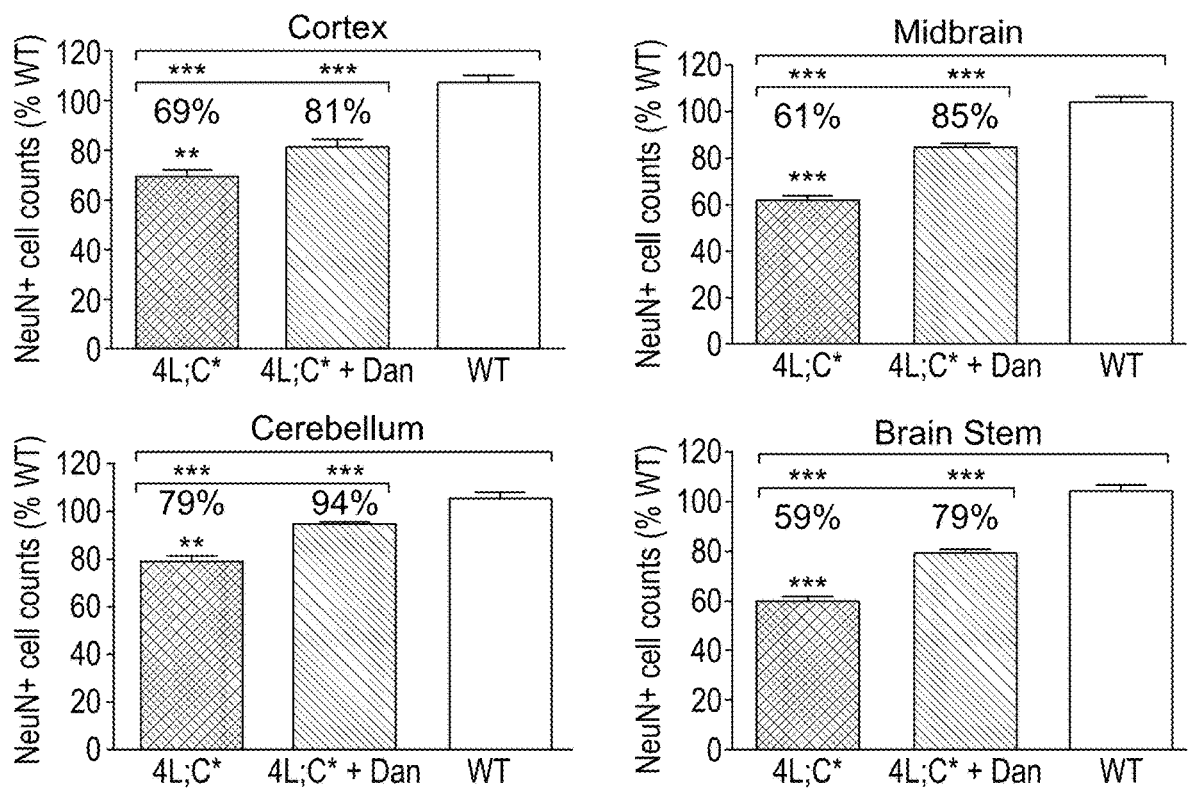

Neurodegeneration in 4L;C* brains were evaluated by counting NeuN positive mature neurons in multiple brain regions (cortex, brain stem, midbrain and cerebellum) from whole sagittal sections (FIG. 4 and FIG. 9). 4L;C* brains had significantly fewer NeuN positive cells (60-80% of WT NeuN+ cells) than WT brains. Treatment with dantrolene resulted in an increase in NeuN positive cells to >80% of WT NeuN+ cells. Decreased NeuN positive cells were observed in cortex, cerebellum, midbrain and brain stem of 4L;C* mice. All of those regions showed an increase in neurons with dantrolene treatment compared to the untreated 4L;C* mice (FIG. 4). These results indicated dantrolene treatment reduced neurodegeneration in 4L;C* mice.

Dantrolene Protects Ryr, Calmodulin and CAMK IV Expression

Figure 5A:
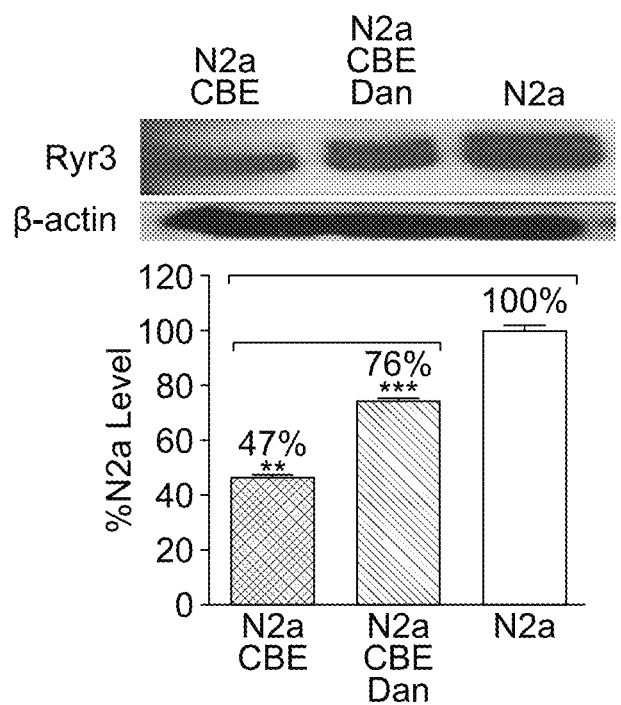
Figure 5B:
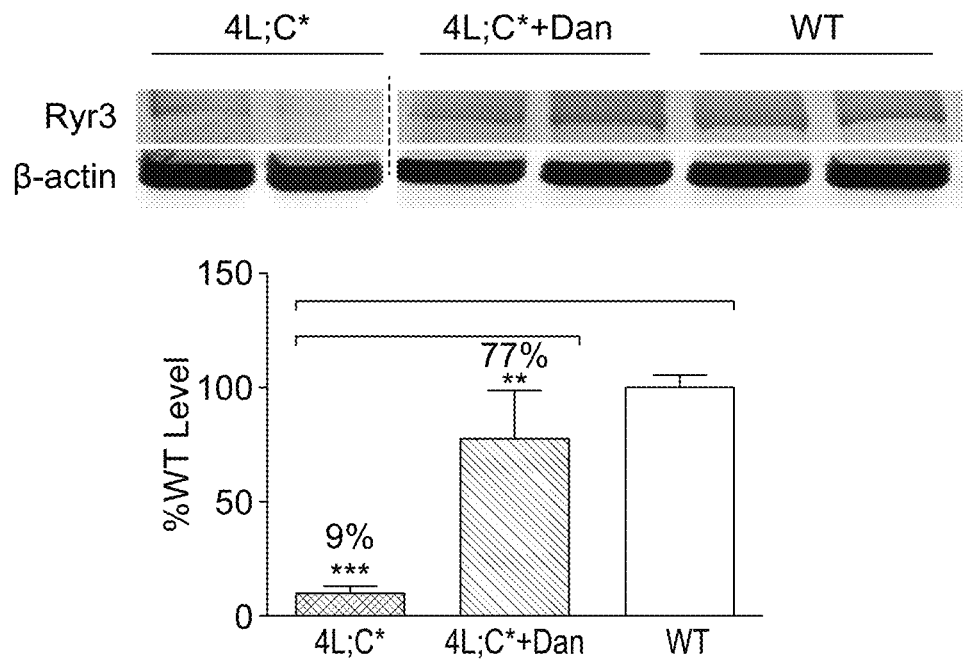
Figure 5C:
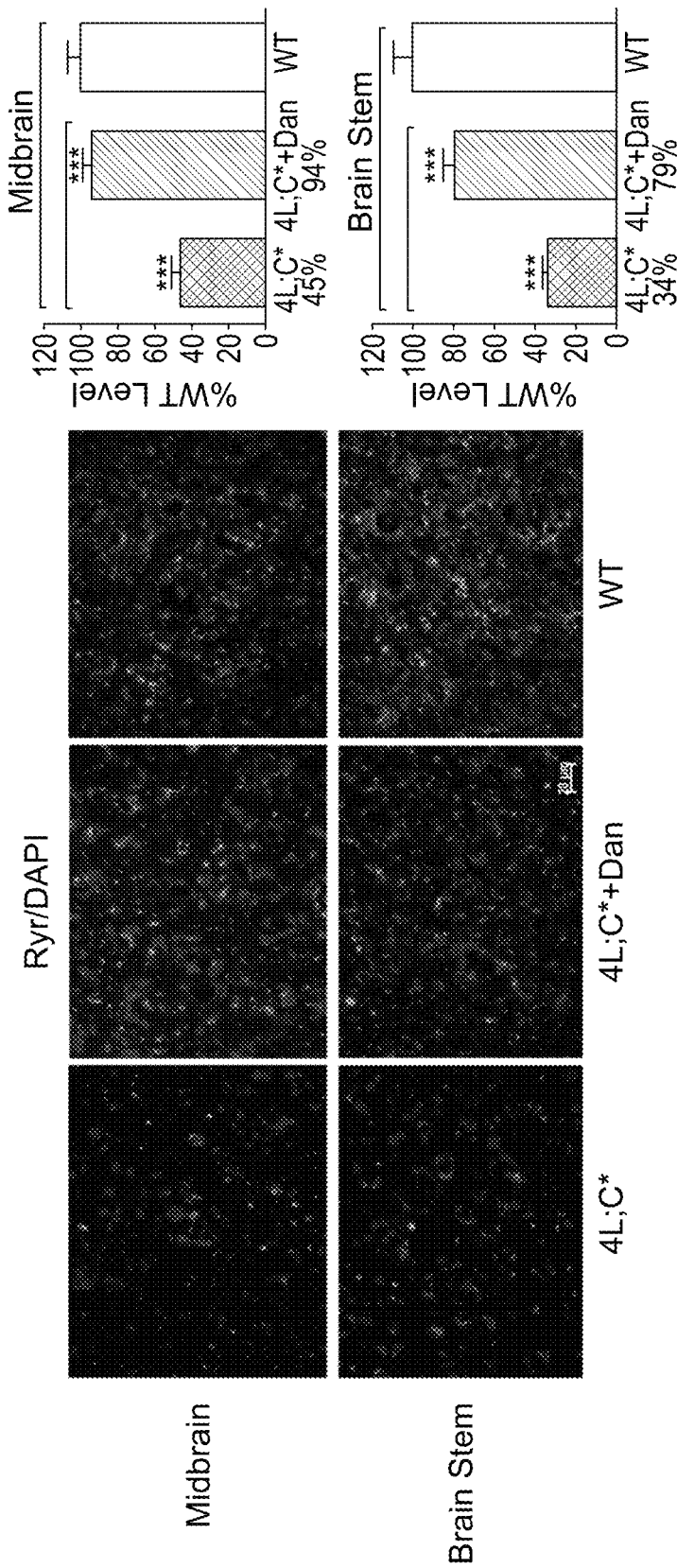
Figure 5D:
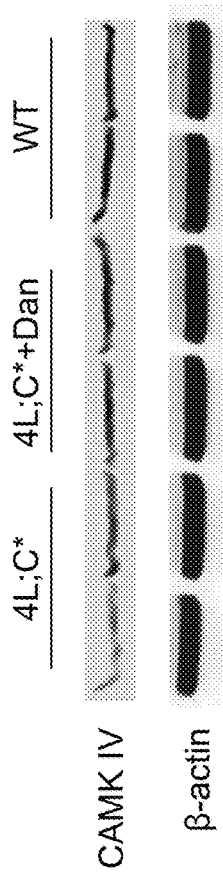
Figure 5D:
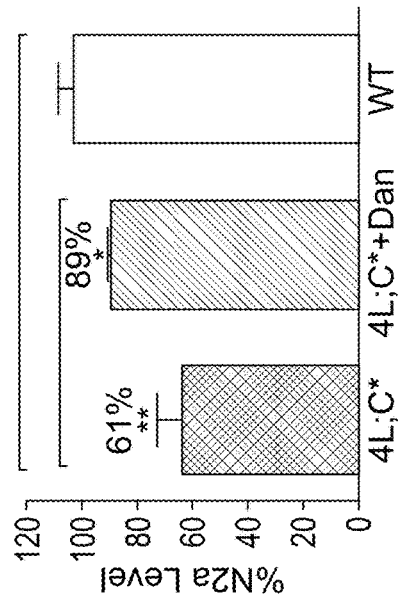
Figure 5E:
Figure 5E:
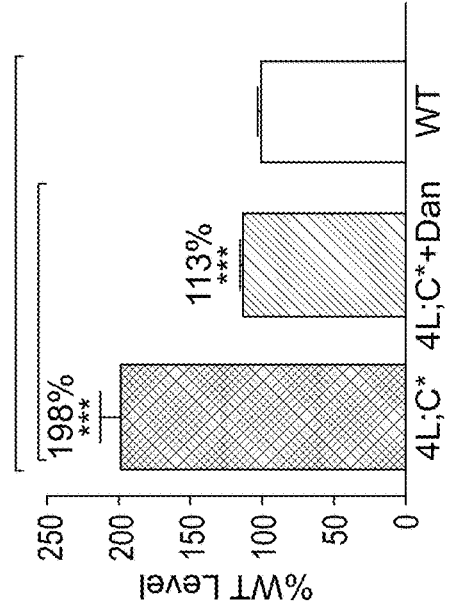
Figure 6:
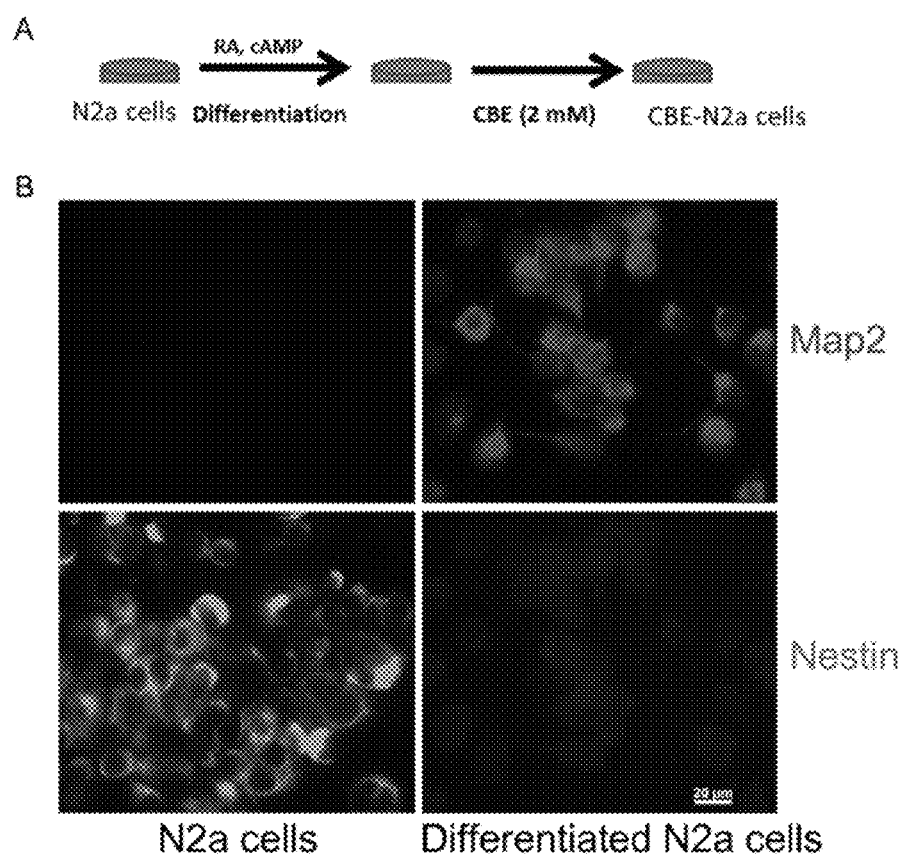

The effect of dantrolene on Ryr protein expression was determined in nGD cells and 4L;C* mouse brains (FIG. 5) Immunoblot analysis showed that Ryr3 protein was reduced to 47% of the WT level in CBE-N2a cells. In dantrolene-treated CBE-N2a cells, levels of Ryr3 were increased to 76% of WT level (FIG. 5A). In 4L;C* mice, Ryr3 was profoundly decreased to just 9% of WT levels in the cerebrum at 44 days of age (FIG. 5B). Dantrolene treatment in 4L;C* mice significantly increased Ryr3 levels to 77% of WT in the cerebrum (FIG. 5B) Immunofluorescence using an anti-Ryr3 antibody confirmed the increase in Ryr signals. In dantrolene treated 4L;C* midbrain (94% of WT) and brain stem (79% of WT) regions (FIG. 5C). Ryr 3 signals were increased in neurons, astrocytes and oligodendrocytes in dantrolene treated 4L;C* mouse brains See Table 1.

TABLE 1

Ryr3 signal levels in brain cells

| | Neuron | Astrocyte | Oligodendrocyte |
|---|---|---|---|
| WT | ++++ | +++ | ++ |
| 4L; C* + Dan | ++ | ++ | + |
| 4L; C* | + | ± | ± |

"+", relative level of immunofluoresence signal of Ryr3 in the mice brain co-stained with Ryr3 and NeuN for neuron, GFAP for astrocyte, or O4 for oligodendrocyte.
Dan, dantrolene.

In the calcium/calmodulin-dependent protein kinase pathway, calmodulin, a calcium sensor protein, binds to calcium and promotes a calcium-dependent kinase activity including CAMK IV (Calcium/calmodulin-dependent protein kinase type IV) for gene expression and biological functions (40). Calmodulin and CAMK IV are potential modulators for Ryr expression. Decreased CAMK IV mRNA and increased calmodulin 2 mRNA have been shown in 4L;C* brains using RNAseq analyses (18). Expression levels of calmodulin and CAMK IV in 4L;C* brains were determined by immunoblot. CAMK IV protein level was reduced to 61% of WT level in untreated 4L;C* cerebrum. With dantrolene treatment, the expression of CAMK IV was increased by 28% (FIG. 5, D). In this study, calmodulin protein was analysed using an anti-Cam antibody that reacts to a class of calmodulins including calmodulin 2. Calmodulin levels were 2 fold above WT levels in 4L;C* brains and were normalized to WT levels with dantrolene treatment (FIG. 5, E). These data suggest that modulating cytosolic calcium levels with dantrolene has protective effects on Ryrs expression as well as proteins involved in the calcium-calmodulin dependent signalling pathway.

Dantrolene Treatment Effects on GCase Function

Modulating ER calcium release promotes chaperone enhancement of GCase stability and trafficking to the lysosome, thereby improving GCase activity (17,41,42). The effect of dantrolene on GCase activity was evaluated in mouse fibroblast cells from Gba1 mutants homozygous for V493L/V394L (4L/4L), D409H/D409H (9H/9H), and D409V/D409V (9V/9V), 4L;C* and WT mice. Dantrolene-treated 4L/4L, 4L;C*, 9H/9H and WT fibroblasts showed significantly increased GCase activity compared to the untreated cells (FIG. 10, A). Dantrolene treated 9V/9V cells did not show an increase in GCase activity.

This result showed that dantrolene promoted GCase activity in select mutants, e.g. V394L and D409H, and WT enzyme.

In vivo effects of dantrolene on GCase function (activity and substrate levels) were analysed in dantrolene treated mouse brains at 44 days of age. The cerebrum was used for GCase activity and cerebellum was used for substrates analysis. Compared to untreated 4L;C*, dantrolene-treated 4L;C* cerebrum showed a 1.2 fold increase in GCase activity which is significantly higher than untreated 4L;C* (FIG. 10, B). However, substrate (GC and GS) concentrations were not reduced in the treated 4L;C* cerebellum (FIG. 10, C). Co-staining for GCase and Lamp1 of mouse brain sections showed a 1.7-fold increased colocalization of GCase within the lysosomes of dantrolene-treated 4L;C* mice compared to untreated 4L;C* brains. However, this level is <40% of Pearson coefficient for WT GCase (FIG. 10, D), indicating <40% mature mutant enzyme trafficked to the lysosomes in dantrolene-treated brains. These results suggest that the effect of dantrolene on GCase activity with the regimen used in this study was not sufficient to translate into significant hydrolytic function for clearance of excess substrates.

DISCUSSION

Currently, there are no effective treatments available for nGD. The goal of the present study was to test the therapeutic potential of a ryanodine receptor antagonist in cell and animal models of nGD. Applicant has shown that dantrolene treatment improves mitochondrial function, protects basal autophagy, delays abnormal gait, and most importantly prolongs survival in nGD mice. Dantrolene prevented the decreased expression of Ryrs in nGD cells and mice, and normalized expression of calmodulin and CAMK IV, key molecules in the calcium/calmodulin-dependent regulation pathway, in mice (40,43,44). Furthermore, dantrolene reduced inflammation and the loss of NeuN+ neurons in mice indicating a compelling neuroprotective effect of treatment. This study shows that modulating ER calcium efflux through Ryrs by dantrolene has therapeutic value for nGD. Neuroprotection by dantrolene is likely through several mechanisms including protection of mitochondrial function, Ryrs expression and autophagy, and enhancement of GCase activity.

Abnormal calcium homeostasis has been implicated in GD (25,45,46). Accumulation of GC causes excess calcium efflux from ER, specifically through Ryrs in neurons in GD (38). Sustained increase in cytosolic calcium accounts for the abnormal cellular function in many lysosomal storage diseases including GD (47), although these changes are not fully understood. Using CBE-N2a cells treated with G6 to inhibit glucosylceramide production, or dantrolene to inhibit calcium efflux through Ryrs, Applicant confirmed that increased cytosolic calcium efflux through Ryrs is mediated by excess substrates, supporting previous findings (25). Most importantly, this new nGD cell model allows further investigation of altered cellular function resulting from disrupted calcium homeostasis.

Ryr protein down-regulation in nGD cells and mouse brains is a novel finding. All three Ryrs are expressed in brain. Ryr1 is predominantly in the skeletal muscle and Ryr2 is mainly in cardiac muscle, whereas Ryr3 is expressed at a low level in a variety of tissues including brain (27,36,48). Decreased expression of Ryrs has been reported in a mouse model of Alzheimer disease that also shows aberrant cellular calcium homeostasis (49). Ryrs protein levels in this study were determined primarily on Ryr3 with a high-quality antibody. Ryr3 was shown to be ubiquitously expressed in the mouse brain. Reduced staining for Ryr3 was found in neurons, astrocytes and oligodendrocytes in 4L;C* mice at end-stage. Normal levels of Ryr3 protein were expressed in 4L;C* brains at 13 days of age, but were reduced to 27% of WT level by the end stage (44 days), suggesting Ryr down-regulation is associated with disease progression and increased substrate accumulation. Thus, Ryr down-regulation is likely caused by substrate accumulation. In 4L;C* mouse brain, substrate levels were higher than that in WT even prior to 13 days, and continued to increase with age (FIG. 10, E). Excess substrate can cause ER-calcium efflux and increases in cytosolic calcium (25). The sustained increase of cytosolic calcium could lead to a feed-back regulation, via calcium dependent transcription regulation pathways, and reduce the expression of Ryrs thereby preventing further calcium efflux from the ER. These results show that blocking ER-calcium release through Ryrs with dantrolene protects Ryr expression, supporting this feedback regulation mechanism. Early intervention before Ryr level reduction would be critical to achieve maximal protection.

Expression of Ryrs can be regulated by the calcium-signalling pathway. In this pathway, calcium and calmodulin binding leads to basal CAMK IV activity which can regulate the expression of Ryrs. Calmodulin bound to calcium is required for the initiation of CAMK-CREB cascade for gene regulation (43,44,50,51). Like many calcium binding proteins, Ryrs have CREB binding elements (52), therefore, their expression is likely regulated by CAMK IV-CREB signalling (53,54). Enhanced expression of calmodulin in 4L;C* brains may reflect increased cytosolic calcium. Reduced CAMK IV mRNA and protein levels in 4L;C* brains suggest that less CAMK IV is available for gene regulation, or decreased transcriptional activity (18,52-54). Excess substrate-mediated calcium release in nGD brains could hinder calcium/calmodulin kinase signalling dependent CREB phosphorylation and lead to reduced Ryrs expression. When nGD mice are treated at an earlier stage with dantrolene (starting at postnatal 5 days) expression of CAMK IV and calmodulin were normalized, highlighting their involvement in the modulating Ryrs expression in nGD. Therefore, protection of Ryrs expression with dantrolene should benefit nGD.

Ryrs down-regulation was concomitant with disease progression. Importantly, the expression of Ryrs was protected by dantrolene. This suggests a role for Ryr in nGD pathogenesis and an attractive target for therapy. Ryrs on ER are key for the regulation of intracellular calcium and an important calcium modulator for neuronal function (49,55). Both ryanodine and dantrolene are antagonists for Ryrs. Ryanodine is toxic to cells making it unsuitable for in vivo studies. In contrast, dantrolene is FDA approved for treatment of malignant hyperthermia (56), readily available, and is distributed in tissues e.g. muscle and liver. It also penetrates the blood-brain barrier to allow for access into the brain (57). Dantrolene is specific to Ryr1 and Ryr3 (58). Blocking Ryrs with dantrolene is associated with improvement in learning and memory performance and protection of synaptic function in neurons in Alzheimer and Huntington disease models (28,32). The significant attenuation of neuropathic phenotype in 4L;C* mice with dantrolene also suggests a clinical benefit for nGD. Impaired calcium homeostasis is a common pathologic factor in glycosphingolipid storage diseases. Specific substrate accumulation causes reduced lysosomal calcium in Niemann-Pick C1 disease and decreased ER calcium in Sandhoff and Niemann-Pick A diseases (59-61). Thus, modulating Ryrs in order to normalize calcium homeostasis could have therapeutic potential for glycosphingolipid storage diseases.

Targeting Ryrs to modulate calcium homeostasis likely acts through multiple mechanisms to achieve neuroprotection in nGD, including protection of mitochondrial function and autophagy, normalizing gene expression/regulation (Ryr), and rescuing mutant GCase activity. Mitochondrial dysfunction is a well-documented pathological feature in nGD (18,62). Inhibition of GCase function by CBE leads to defective mitochondrial function in a human dopaminergic cell line (23). In chronic nGD mouse brains decreased mitochondrial ATP production and oxygen consumption are associated with protein aggregation (a-synuclein and amyloid precursor protein) on mitochondria (21). Impaired respiratory chain and mitochondrial membrane potential has been reported in primary neurons and astrocytes of acute nGD mice (23,62). Reduced mitochondrial function is also a significant feature in 4L;C* mice and in CBE-N2a cells (18). ER and mitochondria are physically and functionally linked with altered calcium homeostasis promoting mitochondrial dysfunction and disruption of the mitochondrial membrane potential (63-65). Furthermore, the role of Ryr in ER calcium and mitochondrial function is supported by a study of the conditional knockout of cardiac Ryr2 in mice (66). Here, depletion of Ryr2 leads to reduced mitochondrial calcium and oxidative metabolism (66). Therefore, modulating calcium homeostasis through Ryrs would have benefits for mitochondrial function. Indeed, in both CBE-N2a cells and 4L;C* mice, dantrolene treatment significantly improved the rate of mitochondrial oxygen consumption and ATP production. These data support the notion that Ryr antagonism may have protective effects on mitochondrial function in nGD.

In many lysosomal storage diseases, defective lysosomal enzyme/protein function interrupts the fusion of the lysosome with the autophagosome for proper degradation of macromolecules (67-70). Abnormal autophagy, either increased or decreased, has been demonstrated in nGD cell and animal models, and patient brain samples (5,20,22). Little is known, however, about the mechanisms regulating autophagy in nGD, although it has been shown that autophagy in general is regulated by cytosolic calcium (71,72). Increased calcium load induced by starvation is known to induce autophagy (71). In this study, LC3-II was used to monitor autophagy. LC3 (microtubule-associated protein 1 light chain 3) has two forms, LC3-I is distributed within the cytoplasm and nucleus and LC3-II conjugates to phosphatidylethanolamine on the autophagosomal membrane. Increased LC3-II reflects an induction of autophagy in response to cellular stress. In the nGD mice, dantrolene treatment significantly reduced LC3-II to WT levels suggesting that autophagy in nGD is regulated by the ER-calcium flux through Ryrs. Thus, modulating cytosolic calcium levels could be a target for maintaining basal autophagy and normal cell function.

Modulation of ER-calcium can regulate calcium-dependent chaperones for GCase protein folding control and proper degradation (17,41,42,73). Inhibition of Ryrs reduces intraluminal calcium levels and enhances the expression of ER chaperone proteins that promote protein folding. Specifically, for mutated GCase L'i44P in fibroblasts, this leads to increased folding and trafficking to the lysosome (17,74). Modulating ER proteostasis by antagonizing Ryr with dantrolene has shown improvement in Niemann-Pick disease by enhanced type C1 protein level and attenuated the cholesterol and sphingolipids in Niemann-Pick type C disease fibroblasts (73). In addition to Ryrs, blocking L type calcium channels (LTCC) also induces chaperone activity on mutant GCase (75). Although diltiazem, an LTCC blocker, improves expression of cellular chaperones and folding of the mutated enzymes in mouse and human fibroblasts (75, 76), it fails to translate to similar changes in animal models of GD (76). In the present study, dantrolene was able to enhance GCase activity in select homozygous Gba1 mutations (V493L/V394L, D409H/D409H), 4L;C* and WT mice fibroblasts. In 4L;C* mouse brains dantrolene enhanced mutant GCase activity and lysosomal localization, however, the level was not sufficient to prevent substrate accumulation. Increasing administration to a daily regimen may achieve better efficacy on GCase hydrolytic function.

This study highlights a profound pathogenic role for Ryrs in nGD and supports a novel strategy to preserve calcium homeostasis in the early stages of nGD and thereby slow disease progression, and demonstrates that targeting Ryrs to modulate calcium homeostasis has neuroprotective potential in nGD by protecting mitochondrial function, normalizing expression of Ryrs, protecting autophagy, enhancing mutant GCase activity and reducing inflammation and neuron loss.

Materials and Methods

Materials

The following were from commercial sources: N2a (ATC-CIO-CCLim-131, VA); CBE (EMD Millipore, Bedford, Mass.); Dantrolene, retinoic acid, dbcAMP and caffeine (Sigma, St. Louis, Mo.); M-PER Mammalian Protein Extraction Reagent, SuperSignalm West Dura ECL detection kit, Pierce BCA protein assay kit (ThermoFisher Sci, Waltham, Mass.). Antibodies: Ryr1, Ryr3, Map2 and Nestin (EMD Millipore, Bedford, Mass.); CAM (calmodulin) (Santa Cruz Biotechnology, Dallas, Tex.); LC3 (Novus, Littleton, Colo.); CAMK IV (calcium/calmodulin-dependent kinase IV) (Abcam, San Francisco, Calif.); CD68 (BD Biosciences, Franklin Lakes, N.J.); NuPAGE Gels (3-8%, 4-12%, 10%, 16%) and Bis-Tris Buffer, Sodium Acetate Buffer, SeaBlue Protein Standard plus, PVDF membrane, iBlot transfer kit, and iBind Cards (Life Technologies. Carlsbad, Calif.); AP colour reagent and AP Conjugate Substrate Kit (Bio-Red, Hercules, Calif.); VECTASHIELD mounting medium containing DAPI (Vector, Burlingame, Calif.); Glass chamber slides (LAB-TEK, Rochester, N.Y.). Genz-161(G6) was provided by Sanofi Genzyme (Cambridge, Mass.).

Cell Culture and Treatment

N2a cells were maintained in DMEM/10% FBS (Gibco) medium. Neuronal differentiation of N2a was carried out in the differentiation medium containing 0.5% FBS, 10 μM retinoic acid, 50 ng/ml GDNF (Alomore lab) and 1 mM dbcAMP in DMEM for 3 days (37). The differentiated N2a cells were treated with 2 mM CBE for 5 days in the differentiation medium. Dantrolene (12.5 μM), ryanodine (10 μM) or G6 (0.8 μM) was added to the CBE-N2a cells and cultured for 5 days. The medium with the reagents was changed every 2 days. The differentiation status of the neuronal cells was confirmed by anti-Map2 (mature neuron) or anti-Nestin (undifferentiated neuronal cells) antibody staining. Cell viability after each drug treatment was measured by CellTiter-Fluoirm Cell Viability assay (Promega). The dose for each compound was determined from CellTiter-Fluor™ Cell Viability assay with >95% viability and endotoxin test of <0.05 EU/ml (GenScript ToxinSenor). The cells were from same passage and treated at the same time for all the experiments.

Calcium Level Measurement

Intracellular calcium levels were determined using the Fura-2 QBT Calcium Kit (Molecular Devices, Sunnyvale, Calif.) on 96 well plates by M5 SpectraMax plate reader (Molecular Devices). N2a cells were seeded in each well (20,000/well) with differentiation medium (0.5% FBS, DMEM, 10 AM retinoic acid, 1 mM dbcAMP) for 72 h (37). The differentiated N2a cells were cultured with DMEM medium with 10% FBS containing CBE (2 mM) for 5 days, followed by treatment with different combinations of dantrolene (12.5 μM), ryanodine (10 μM) and G6 (0.8 μM) for a further 5 days. The cell medium was replaced every two days. The treated cells were incubated with Fura-2 QBT dye at 37 C for 1 h for Fura-2 QBT uptake (Fura2 QBT® calcium kit protocol, Molecular Devices). Caffeine (10 mM) was used as an ER calcium efflux stimulant in the assay (38,39). The plate reader setting was 340/380 nm (excitation) and 510 nm (emission). Baseline calcium levels were measured prior to caffeine addition (−30 s). Cytosolic calcium levels were recorded every 30 s for duration of 300 s after addition of caffeine. Relative cytosolic calcium levels were determined with the values at 300 s endpoint minus Os baseline. Relative cytosolic calcium level [Fura-2 AF/F (340/380510 nm] for control or treated cells was calculated by Fura-2 fluorescence unit (FU) measured at 340 nm/510 nm (AF=RFU/340 at 300 s end point minus baseline RFU/340 at 0 s) divided by FU at 380 nm/510 nm (F=RFU/380 at 300 s-baseline RFU/380 at 0 s) (Fura2 QBT® calcium kit protocol, Molecular Devices) and normalized to protein level in cells. Data were collected and analysed by SoftMax Pro software (Molecular Devices) and graphical charts were generated by Graphpad Prism 6.0.

Mice and Treatment

4L;C* mice were generated by backcrossing of V394L/V394L Gba1 (4L) and saposin C−/− (C) homozygosity as described previously (33). The strain background of 4L;C* mice was C57BL/6J:129SvEv. Strain- and age-matched WT mice and non-4L;C* littermates (no neurological phenotype) were included as controls. All mice were housed under pathogen-free conditions in an animal facility according to IACUC approved protocols at Cincinnati Children's Hospital Medical Center (CCHMC).

The 4L;C* mice and non-4L;C* littermates were treated with Dantrolene sodium (Revonto® US WorldMeds, Louisville, Ky.) starting at postnatal day 5 by IP injection at 10 mg/kg, three days per week. Mouse body weight was recorded before each injection. Control mice received vehicle (mannitol, APP Pharmaceuticals, Schaumburg, Ill.) injections or no injection at all. The mice were monitored for survival and gait impairments during the treatment.

Gait Analysis

Progression of the neurobehavioural phenotype was assessed by gait analysis to determine sensorimotor function (77,78). Mice were trained to walk through a narrow alley leading into their home-cage. Once trained, paper was placed along the alley floor and the hind paws of each mouse were brushed with nontoxic paint. The mice were then placed at the beginning of the alley. As they walked into their home-cage they left their paw prints on the paper underneath. Stride length and width were determined by measuring the distance between hind paw prints. The 4L;C* and control mice, untreated and non-4L;C* littermates were tested for gait at 30 and 40 days of age.

RNAseq Analyses

Expression of Ryr mRNAs in 4L;C* brain regions (cortex, cerebellum, midbrain and brain stem) was analysed by RNAseq as described previously (18).

Immunohistochemistry and Immunofluorescence

Mouse brains were collected after transcardial perfusion with saline. Half of the brain (sagittal cut) was fixed in 4% paraformaldehyde (PFA) for processing as frozen blocks. CD68 monoclonal antibody staining was performed as previously described (33) using The BenchMark XT IHC/ISH Staining Module (Ventana Medical System, Tucson, Ariz.) at CCHMC Pathology Research Core. Fixed sections were counterstained with hematoxylin. The sections were then scanned by AperioImageScope v2. The CD68 signal was quantified using Image J FIJI (79).

Immunofluorescence staining was performed on PFA fixed brains. The brain sections were incubated in 0.3% Triton X-100 for 30 min, and treated with 50 mM NH4Cl in 1×PBS for 15 min followed by 1×PBS wash. The sections were blocked for 1 hr at RT in Blocking buffer (10% goat serum and 0.4% Triton X-100 in PBS). Rabbit anti-Ryr 1 antibody (1:100) was diluted in the blocking solution and incubated overnight at 4° C. After washing in PBS (3×10 min), the secondary antibody goat anti-rabbit conjugated with Alexa Fluor® 488 (1:1500) in blocking buffer was applied to the sections and incubated for 2 hrs at RT. Mouse anti-Ryr 3 antibody (1:100) and goat anti-mouse conjugated with Alexa Fluor® 488 (1:1500) were used for Ryr 3 detection. For co-staining of neural cells with Ryr3, mouse anti-NeuN antibody (1:500, Millipore), mouse anti-GFAP (1:100, Millipore) or mouse anti-04 (1:100, Millipore) with goat anti-mouse conjugated Alexa Fluor® 594 (1:1000) were used for NeuN, GFAP, or 04 detection, respectively. Rabbit anti-Ryr 3 (1:250, Millipore) with goat anti-rabbit conjugated Alexa Fluor® 488 (1:1000) were used for Ryr3. Lysosomal localization of GCase was determined using rabbit anti-mouse GCase (1:50) antibody (15) with goat anti-rabbit conjugated Alexa Fluor® 488 (1:1000) for mouse GCase detection. Rat anti-Lamp1 (1:100, RDI) and rabbit anti-rat IgG conjugated Texas Red (1:1000, Abcam) were used for Lamp1 detection. Sections were mounted with VECTASHIELD mounting medium containing DAPI (Vector H1200). Fluorescence signals were visualized and captured by Zeiss Axiovert 200 M microscopy equipped with an Apotome. Pearson correlation coefficient software is incorporated in Apotome microscope and used to analyse the co-localization of two signals (GCase and Lamp1) in cells. The average Pearson correlation coefficient number (from 0 to 1) was derived from the cells in multiple images (21). For counting NeuN$^+$ neurons, mouse anti-NeuN antibody (1:500, Millipore) was applied to brain sections followed by secondary antibody conjugated with FITC. The images of NeuN$^+$ cells in brain sections were acquired by Nikon C2 plus confocal microscope with NIS image stitching function for large image capture in ND acquisition. All NIS images in 32 bit were converted into 16 bit format and analysed by ImageJ FIJI. NeuN$^+$ cells were counted from whole brain images and from multiple images (3.5×2.0 mm) in each brain region (cortex, midbrain, cerebellum and brain stem).

For cell culture immunostaining differentiated N2a cells were seeded on chamber slides and stained with anti-Map2 antibody (1:200) followed by the protocol described above except for using 3% BSA in PBS as blocking buffer. Fluorescent images were processed by Zeiss Apotome 200M.

Immunoblot

Half of mice brain (sagittal cut) tissues were homogenized in M-PER Mammalian Protein Extraction Reagent and subjected to electrophoresis. Ryr proteins (~500 kD) in tissues lysate were separated on 3-8% NuPAGE gel running at 90V for 12 h at 4° C. in acetate buffer. 13-actin was resolved on 4-12% Bis-Tris gel. The proteins were transferred to PVDF membrane using iBlot 2 gel transfer device following manufacturer's instructions. The blots were incubated with anti-mouse Ryr3 monoclonal antibody (1/250) or anti-13-actin (1:5000) overnight at 4° C. in 1.5% BSA/1.5% milk/PBS buffer. LC3, CAMK IV and calmodulin were separated on 16% Tris-glycine gel (Novex) and detected by anti-LC3 (1:1000), anti-CAMK IV (1:500) or anti-CAM (1:1000), respectively. The signals were detected with either ECL detection reagent or AP Conjugate Substrate Kit according to manufacturer's instructions. Band intensities on immunoblots were quantitated by Image J (NIH, Baltimore, Va.).

Seahorse Mitochondrial Function Assay

Cultured N2a cells treated with or without CBE, dantrolene or G6 were transferred to a XF96 assay plate at 10,000 cells/well and allowed to grow overnight in DMEM medium containing 10% FBS with each compound as described above in Cell culture and treatment section. Cell numbers were determined using a haemocytometer. Prior to mitochondrial function assay on XF96 Extracellular Flux Analyzers (Seahorse Biosciences), the cells in the wells of XF96 assay plates were washed by gently adding warm assay medium to the side of each well. The plates were transferred to a 37° C. incubator without $CO_2$ for 30-60 min before the addition of XF assay medium (Seahorse Bioscience) containing 25 mM glucose and 1 mM pyruvate. After calibration of the Analyzer, the plate was sequentially injected with A: 25 µl of 8 µM oligomycin, B: 25 µl of 27 µM cyanide-p-trifluoromethoxyphenylhydrazone (FCCP), and C: 25 µl of 50 µM antimycin A. Oxygen consumption rate (OCR) was measured, and the data were analysed using the XFe Wave software. The respiration parameters were calculated by subtracting the average respiration rates before and after the addition of the electron transport inhibitors: oligomycin, FCCP and antimycin A. The parameters include basal respiration (baseline respiration minus antimycin A post injection respiration), ATP production (baseline respiration minus oligomycin post injection respiration), and maximal respiratory (FCCP stimulated respiration minus antimycin A post injection respiration). Cell mitochondrial function presented as respiration parameters that were normalized by cell numbers (39).

Brain mitochondria were isolated from 4L;C, WT, and dantrolene treated 4L;C mice as described with slight modifications (21,80). Mouse brain tissues were digested with trypsin for 30 min on ice followed by homogenization on the gentle MACS Dissociator using Program m_mito_tissues_01 (MACS, Miltenyi Biotec). Homogenates were suspended in 4 ml ice-cold buffer (1.0 mM KCl, 1.0 mM Tris-HCl, and 0.1 mM EDTA, pH 8.0) and mixed with 0.67 ml of 2 M sucrose. The suspension was centrifuged at 1300×g for 5 min to remove nuclei, unbroken cells and large membrane fragments. The supernatant containing mitochondria were pelleted after centrifugation at 9600×g for 10 min at 4° C. The mitochondrial pellet was resuspended in the Storage Buffer (MACS, Miltenyi Biotec). Total mitochondrial protein was determined using Bradford Assay reagent (Bio-Rad). ATP production rates were determined with isolated mitochondria using XF96 Extracellular Flux Analyzers. The mitochondria were diluted in cold 1×MAS (Mitochondria' Assay Solution) and substrate (pyruvate/malate) (Seahorse Biosciences). The mitochondrial suspension (20 µg mitochondrial proteins in 25 µl) was aliquoted into each well while the plate was on ice. The plate was then centrifuged using a swinging bucket microplate adaptor at 2000×g for 20 min at 4° C. To start the assay, 155 µl of pre-warmed (37° C.) 1×MAS and substrate were added to each well containing isolated mitochondria and incubated at 37° C. with no $CO_2$ for 10 min. After calibration of the Analyzer, the plate containing mitochondria was sequentially injected with A: port A, 20 µl of 40 mM ADP (4 mM, final); port B, 22 µl of 25 µg/ml oligomycin (2.5 µg/ml, final); port C, 24 µl of 40 µM FCCP (4 µM, final); and port D, 26 µl of 40 µM antimycin A (4 µM, final). OCR was measured and the data were analysed using the XFe Wave software as described above. ATP production rate in brain mitochondria was normalized to mg of mitochondrial protein (18).

GCase Activity Analyses

Cells were homogenized in 1% sodium taurocholate/1% Triton X-100. GCase activity was determined fluorometrically using 4MU-Glucose as the substrate in 0.25% sodium taurocholate, 0.25% Triton X-100 and 0.1M citric-phosphate buffer (pH 5.6) as 5.

described previously (81). Brain tissues were homogenized in 1×PBS and incubated in 5 µM brain phosphatidylserine and 0.1M citric-phosphate buffer (pH 5.6) for GCase activity assay using 4MU-Glucose as substrate (82). Protein concentrations were determined by BCA assay using BSA as standard.

Glycosphingolipid Analyses

Glycosphingolipids in mouse brains and N2a cells were extracted with chloroform and methanol as described (83). GC and GS content in the extracts was analysed by ESI-LC-MS/MS using a Waters Quattro Micro API triple quadrupole mass spectrometer (Milford, Mass.) interfaced with Acquity UPLC system as described (35). The concentration of GC and GS in the brain was normalized to mg tissue weight and in the cells was normalized by mg protein in the cell lysate.

Statistical Analyses

The data are presented as mean±SEM and were analysed by Student's t-test or one-way ANOVA with post-hoc Tukey test using GraphPad Prism 6. The level of significance was set at $P<0.05$. Survival analysis was performed using Kaplan-Meier and the Mantel-Cox tests.

REFERENCES

1 Grabowski, G. A., Petsko, G. A. and Kolodny, E. H. (2010) Valle, D., Beaudet, A., Vogelstein, B., Kinzler, K. W., Antonarakis, S. E., Ballabio, A., Scriver, C. R., Sly, W. S., Childs, B., Bunz, F., Gibson, K. M. and Mitchell, G. (eds.), In The Online Metabolic and Molecular Bases of Inherited Diseases. The McGraw-Hill Companies, Inc., New York.

2 Nilsson, O. and Svennerholm, L. (1982) Accumulation of glucosylceramide and glucosylsphingosine (psychosine) in cerebrum and cerebellum in infantile and juvenile Gaucher disease. J. Neurochem. 39, 709-718.

3 Orvisky, E., Park, J. K., LaMarca, M. E., Ginns, E. I., Martin, B. M., Tayebi, N. and Sidransky, E. (2002) Glucosylsphingosine accumulation in tissues from patients with Gaucher disease: correlation with phenotype and genotype. Mol. Genet. Metab. 76, 262-270.

4 Kaye, E. M., Ullman, M. D., Wilson, E. R. and Barranger, J. A. (1986) Type 2 and type 3 Gaucher disease: a morphological and biochemical study. Ann. Neurol. 20, 223-230.

5 Burrow, T. A., Sun, Y., Prada, C. E., Bailey, L., Zhang, W., Brewer, A., Wu, S. W., Setchell, K. D., Witte, D., Cohen, M. B. et al. (2014) CNS, lung, and lymph node involvement in Gaucher disease type 3 after 11 years of therapy: Clinical, histopathologic, and biochemical findings. Mol. Genet. Metab.

6 Conradi, N. G., Sourander, P., Nilsson, O., Svennerholm, L. and Erikson, A. (1984) Neuropathology of the Norrbottnian type of Gaucher disease. Morphological and biochemical studies. Acta Neuropathol. 65, 99-109.

7 Tantawy, A. A., Sherif, E. M., Adly, A. A., Hassanine, S. and Awad, A. H. (2013) Evoked potentials and neurocognitive functions in pediatric Egyptian Gaucher patients on enzyme replacement therapy: a single center experience. J. Inherit. Metab. Dis. 36, 1025-1037.

8 Kuter, D. J., Mehta, A., Hollak, C. E., Giraldo, P., Hughes, D., Belmatoug, N., Brand, M., Muller, A., Schaaf, B., Giorgino, R. et al. (2013) Miglustat therapy in type 1 Gaucher disease: clinical and safety outcomes in a multicenter retrospective cohort study. Blood Cells Mol. Dis. 51, 116-124.

9 Lukina, E., Watman, N., Dragosky, M., Pastores, G. M., Arreguin, E. A., Rosenbaum, H., Zimran, A., Angell, J., Ross, L., Puga, A. C. et al. (2014) Eliglustat, an investigational oral therapy for Gaucher disease type 1: Phase 2 trial results after 4 years of treatment. Blood Cells Mol. Dis. 53, 274-276.

10 Ashe, K. M., Bangari, D., Li, L., Cabrera-Salazar, M. A., Bercury, S. D., Nietupski, J. B., Cooper, C. G., Aerts, J. M., Lee, E. R., Copeland, D. P. et al. (2011) Iminosugar-based inhibitors of glucosylceramide synthase increase brain glycosphingolipids and survival in a mouse model of Sandhoff disease. PLoS One. 6, e21758.

11 Nietupski, J. B., Pacheco, J. J., Chuang, W. L., Maratea, K., Li, L., Foley, J., Ashe, K. M., Cooper, C. G., Aerts, J. M., Copeland, D. P. et al. (2012) Iminosugar-based inhibitors of glucosylceramide synthase prolong survival but paradoxically increase brain glucosylceramide levels in Niemann-Pick C mice. Mol. Genet. Metab. 105, 621-628.

12 Williams, I. M., Wallom, K. L., Smith, D. A., Al Eisa, N., Smith, C. and Platt, F. M. (2014) Improved neuroprotection using miglustat, curcumin and ibuprofen as a triple combination therapy in Niemann-Pick disease type C1 mice. Neurobiol. Dis. 67C, 9-17.

13 Cabrera-Salazar, M. A., Deriso, M., Bercury, S. D., Li, L., Lydon, J. T., Weber, W., Pande, N., Cromwell, M. A., Copeland, D., Leonard, J. et al. (2012) Systemic delivery of a glucosylceramide synthase inhibitor reduces CNS substrates and increases lifespan in a mouse model of type 2 Gaucher disease. PLoS One. 7, e43310.

14 Marshall, J., Sun, Y., Bangari, D. S., Budman, E., Park, H., Nietupski, J. B., Allaire, A., Cromwell, M. A., Wang, B., Grabowski, G. A. et al. (2016) CNS-accessible Inhibitor of Glucosylceramide Synthase for Substrate Reduction Therapy of Neuronopathic Gaucher Disease. Mol. Ther. 24, 1019-1029.

15 Sun, Y., Ran, H., Liou, B., Quinn, B., Zamzow, M., Zhang, W., Bielawski, J., Kitatani, K., Setchell, K. D., 15 Hannun, Y. A. et al. (2011) Isofagomine in vivo effects in a neuronopathic Gaucher disease mouse. PLoS One. 6, e19037.

16 Vitner, E. B., Salomon, R., Farfel-Becker, T., Meshcheriakova, A., Ali, M., Klein, A. D., Platt, F. M., Cox, T. M. and Futerman, A. H. (2014) RIPK3 as a potential therapeutic target for Gaucher's disease. Nat. Med. 20, 204-208.

17 Wang, F., Agnello, G., Sotolongo, N. and Segatori, L. (2011) Ca2+ homeostasis modulation enhances the amenability of L444P glucosylcerebrosidase to proteostasis regulation in patient-derived fibroblasts. ACS Chem. Biol. 6, 158-168.

18 Dasgupta, N., Xu, Y. H., Li, R., Peng, Y., Pandey, M. K., Tinch, S. L., Liou, B., Inskeep, V., Zhang, W., Setchell, K. D. et al. (2015) Neuronopathic Gaucher disease: dysregulated mRNAs and miRNAs in brain pathogenesis and effects of pharmacologic chaperone treatment in a mouse model. Hum. Mol. Genet.

19 Wong, K., Sidransky, E., Verma, A., Mixon, T., Sandberg, G. D., Wakefield, L. K., Morrison, A., Lwin, A., Colegial, C., Allman, J. M. et al. (2004) Neuropathology provides clues to the pathophysiology of Gaucher disease. Mol. Genet. Metab. 82, 192-207.

20 Sun, Y. and Grabowski, G. A. (2010) Impaired autophagosomes and lysosomes in neuronopathic Gaucher disease. Autophagy. 6, 648-649.

21 Xu, Y. H., Xu, K., Sun, Y., Liou, B., Quinn, B., Li, R. H., Xue, L., Zhang, W., Setchell, K. D., Witte, D. et al. (2014) Multiple pathogenic proteins implicated in neuronopathic Gaucher disease mice. Hum. Mol. Genet. 23, 3943-3957.

22 Osellame, L. D., Rahim, A. A., Hargreaves, I. P., Gegg, M. E., Richard-Londt, A., Brandner, S., Waddington, S. N., Schapira, A. H. and Duchen, M. R. (2013) Mitochondria and quality control defects in a mouse model of Gaucher disease—links to Parkinson's disease. Cell Metab. 17, 941-953.

23 Cleeter, M. W., Chau, K. Y., Gluck, C., Mehta, A., Hughes, D. A., Duchen, M., Wood, N. W., Hardy, J., Mark Cooper, J. and Schapira, A. H. (2013) Glucocerebrosidase inhibition causes mitochondrial dysfunction and free radical damage. Neurochem. Int. 62, 1-7.

24 Mazzulli, J. R., Xu, Y. H., Sun, Y., Knight, A. L., McLean, P. J., Caldwell, G. A., Sidransky, E., Grabowski, G. A. and Krainc, D. (2011) Gaucher disease glucocerebrosidase and alpha-synuclein form a bidirectional pathogenic loop in synucleinopathies. Cell. 146, 37-52.

25 Pelled, D., Trajkovic-Bodennec, S., Lloyd-Evans, E., Sidransky, E., Schiffmann, R. and Futerman, A. H. (2005) Enhanced calcium release in the acute neuronopathic form of Gaucher disease. Neurobiol. Dis. 18, 83-88.

26 Krause, T., Gerbershagen, M. U., Fiege, M., Weisshorn, R. and Wappler, F. (2004) Dantrolene—a review of its pharmacology, therapeutic use and new developments. Anaesthesia. 59, 364-373.

27 Giannini, G. and Sorrentino, V. (1995) Molecular structure and tissue distribution of ryanodine receptors calcium channels. Med. Res. Rev. 15, 313-323.

28 Oules, B., Del Prete, D., Greco, B., Zhang, X., Lauritzen, I., Sevalle, J., Moreno, S., Paterlini-Brechot, P., Trebak, M., Checler, F. et al. (2012) Ryanodine receptor blockade reduces amyloid-beta load and memory impairments in Tg2576 mouse model of Alzheimer disease. J. Neurosci. 32, 11820-11834.

29 Chakroborty, S., Briggs, C., Miller, M. B., Goussakov, I., Schneider, C., Kim, J., Wicks, J., Richardson, J. C., Conklin, V., Cameransi, B. G. et al. (2012) Stabilizing ER Ca2+ channel function as an early preventative strategy for Alzheimer's disease. PLoS One. 7, e52056.

30 Popescu, B. O., Oprica, M., Sajin, M., Stanciu, C. L., Bajenaru, O., Predescu, A., Vidulescu, C. and Popescu, L. M. (2002) Dantrolene protects neurons against kainic acid induced apoptosis in vitro and in vivo. J. Cell Mol. Med. 6, 555-569.

31 Ferreiro, E., Oliveira, C. R. and Pereira, C. (2004) Involvement of endoplasmic reticulum Ca2+ release through ryanodine and inositol 1,4,5-triphosphate receptors in the neurotoxic effects induced by the amyloid-beta peptide. J. Neurosci. Res. 76, 872-880.

32 Chen, X., Wu, J., Lvovskaya, S., Herndon, E., Supnet, C. and Bezprozvanny, I. (2011) Dantrolene is neuroprotective in Huntington's disease transgenic mouse model. Mol. Neurodegener. 6, 81.

33 Sun, Y., Liou, B., Ran, H., Skelton, M. R., Williams, M. T., Vorhees, C. V., Kitatani, K., Hannun, Y. A., Witte, D. P., Xu, Y. H. et al. (2010) Neuronopathic Gaucher disease in the mouse: viable combined selective saposin C deficiency and mutant glucocerebrosidase (V394L) mice with glucosylsphingosine and glucosylceramide accumulation and progressive neurological deficits. Hum. Mol. Genet. 19, 1088-1097.

34 Burrow, T. A., Sun, Y., Prada, C. E., Bailey, L., Zhang, W., Brewer, A., Wu, S. W., Setchell, K. D., Witte, D., Cohen, M. B. et al. (2015) CNS, lung, and lymph node involvement in Gaucher disease type 3 after 11 years of therapy: Clinical, histopathologic, and biochemical findings. Mol. Genet. Metab. 114, 233-241.

35 Sun, Y., Zhang, W., Xu, Y. H., Quinn, B., Dasgupta, N., Liou, B., Setchell, K. D. and Grabowski, G. A. (2013) Substrate compositional variation with tissue/region and Gba1 mutations in mouse models—implications for Gaucher disease. PLoS One. 8, e57560.

36 Bouchard, R., Pattarini, R. and Geiger, J. D. (2003) Presence and functional significance of presynaptic ryanodine receptors. Prog. Neurobiol. 69, 391-418.

37 Tremblay, R. G., Sikorska, M., Sandhu, J. K., Lanthier, P., Ribecco-Lutkiewicz, M. and Bani-Yaghoub, M. (2010) Differentiation of mouse Neuro 2A cells into dopamine neurons. J. Neurosci. Methods. 186, 60-67.

38 Korkotian, E., Schwarz, A., Pelled, D., Schwarzmann, G., Segal, M. and Futerman, A. H. (1999) Elevation of intracellular glucosylceramide levels results in an increase in endoplasmic reticulum density and in functional calcium stores in cultured neurons. J. Biol. Chem. 274, 21673-21678.

39 Alonso, M. T., Chamero, P., Villalobos, C. and Garcia-Sancho, J. (2003) Fura-2 antagonises calcium-induced calcium release. Cell Calcium. 33, 27-35.

40 Soderling, T. R. (1999) The Ca-calmodulin-dependent protein kinase cascade. Trends Biochem. Sci. 24, 232-236.

41 Mu, T. W., Fowler, D. M. and Kelly, J. W. (2008) Partial restoration of mutant enzyme homeostasis in three distinct lysosomal storage disease cell lines by altering calcium homeostasis. PLoS Biol. 6, e26.

42 Ong, D. S., Mu, T. W., Palmer, A. E. and Kelly, J. W. (2010) Endoplasmic reticulum Ca2+ increases enhance mutant glucocerebrosidase proteostasis. Nat. Chem. Biol. 6, 424-432.

43 Chow, F. A., Anderson, K. A., Noeldner, P. K. and Means, A. R. (2005) The autonomous activity of calcium/calmodulin-dependent protein kinase IV is required for its role in transcription. J. Biol. Chem. 280, 20530-20538.

44 Fruen, B. R., Bardy, J. M., Byrem, T. M., Strasburg, G. M. and Louis, C. F. (2000) Differential Ca(2+) sensitivity of skeletal and cardiac muscle ryanodine receptors in the presence of calmodulin. Am. J. Physiol. Cell Physiol. 279, C724-733.

45 Kilpatrick, B. S., Magalhaes, J., Beavan, M. S., McNeill, A., Gegg, M. E., Cleeter, M. W., Bloor-Young, D., Churchill, G. C., Duchen, M. R., Schapira, A. H. et al. (2015) Endoplasmic reticulum and lysosomal Ca stores are remodelled in GBA1-linked Parkinson disease patient fibroblasts. Cell Calcium.

46 Schondorf, D. C., Aureli, M., McAllister, F. E., Hindley, C. J., Mayer, F., Schmid, B., Sardi, S. P., Valsecchi, M., Hoffmann, S., Schwarz, L. K. et al. (2014) iPSC-derived neurons from GBA1-associated Parkinson's disease patients show autophagic defects and impaired calcium homeostasis. Nat. Commun. 5, 4028.

47 Kiselyov, K., Yamaguchi, S., Lyons, C. W. and Muallem, S. (2010) Aberrant Ca2+ handling in lysosomal storage disorders. Cell Calcium. 47, 103-111.

48 Furuichi, T., Furutama, D., Hakamata, Y., Nakai, J., Takeshima, H. and Mikoshiba, K. (1994) Multiple types of ryanodine receptor/Ca2+ release channels are differentially expressed in rabbit brain. J. Neurosci. 14, 4794-4805.

49 Del Prete, D., Checler, F. and Chami, M. (2014) Ryanodine receptors: physiological function and deregulation in Alzheimer disease. Mol. Neurodegener. 9, 21.

50 Ozawa, T. (2010) Modulation of ryanodine receptor Ca2+ channels (Review). Mol. Med. Rep. 3, 199-204.

51 Malik, Z. A., Stein, I. S., Navedo, M. F. and Hell, J. W. (2014) Mission CaMKIIgamma: shuttle calmodulin from membrane to nucleus. Cell. 159, 235-237.

52 Zhang, X., Odom, D. T., Koo, S. H., Conkright, M. D., Canettieri, G., Best, J., Chen, H., Jenner, R., Herbolsheimer, E., Jacobsen, E. et al. (2005) Genome-wide analysis of cAMP-response element binding protein occupancy, phosphorylation, and target gene activation in human tissues. Proc. Natl. Acad. Sci. USA. 102, 4459-4464.

53 Bito, H., Deisseroth, K. and Tsien, R. W. (1996) CREB phosphorylation and dephosphorylation: a Ca(2+)- and stimulus duration-dependent switch for hippocampal gene expression. Cell. 87, 1203-1214.

54 Bading, H., Ginty, D. D. and Greenberg, M. E. (1993) Regulation of gene expression in hippocampal neurons by distinct calcium signaling pathways. Science. 260, 181-186.

55 Adasme, T., Haeger, P., Paula-Lima, A. C., Espinoza, I., Casas-Alarcon, M. M., Carrasco, M. A. and Hidalgo, C. (2011) Involvement of ryanodine receptors in neurotrophin-induced hippocampal synaptic plasticity and spatial memory formation. Proc. Natl. Acad. Sci. USA. 108, 3029-3034.

56 Muehlschlegel, S. and Sims, J. R. (2009) Dantrolene: mechanisms of neuroprotection and possible clinical applications in the neurointensive care unit. Neurocrit. Care. 10, 103-115.

57 Enokizono, J., Kusuhara, H., Ose, A., Schinkel, A. H. and Sugiyama, Y. (2008) Quantitative investigation of the role of breast cancer resistance protein (Bcrp/Abcg2) in limiting brain and testis penetration of xenobiotic compounds. Drug Metab. Dispos. 36, 995-1002.

58 Fruen, B. R., Mickelson, J. R. and Louis, C. F. (1997) Dantrolene inhibition of sarcoplasmic reticulum Ca2+ release by direct and specific action at skeletal muscle ryanodine receptors. J. Biol. Chem. 272, 26965-26971.

59 Lloyd-Evans, E., Morgan, A. J., He, X., Smith, D. A., Elliot-Smith, E., Sillence, D. J., Churchill, G. C., Schuchman, E. H., Galione, A. and Platt, F. M. (2008) Niemann-Pick disease type C1 is a sphingosine storage disease that causes deregulation of lysosomal calcium. Nat. Med. 14, 1247-1255.

60 Pelled, D., Lloyd-Evans, E., Riebeling, C., Jeyakumar, M., Platt, F. M. and Futerman, A. H. (2003) Inhibition of calcium uptake via the sarco/endoplasmic reticulum Ca2+-ATPase in a mouse model of Sandhoff disease and prevention by treatment with N-butyldeoxynojirimycin. J. Biol. Chem. 278, 29496-29501.

61 Ginzburg, L. and Futerman, A. H. (2005) Defective calcium homeostasis in the cerebellum in a mouse model of Niemann-Pick A disease. J. Neurochem. 95, 1619-1628.

62 Osellame, L. D. and Duchen, M. R. (2013) Defective quality control mechanisms and accumulation of damaged mitochondria link Gaucher and Parkinson diseases. Autophagy. 9, 1633-1635.

63 Mbaya, E., Oules, B., Caspersen, C., Tacine, R., Massinet, H., Pennuto, M., Chretien, D., Munnich, A., Rotig, A., Rizzuto, R. et al. (2010) Calcium signalling-dependent mitochondrial dysfunction and bioenergetics regulation in respiratory chain Complex II deficiency. Cell Death Differ. 17, 1855-1866.

64 Denton, R. M. (2009) Regulation of mitochondrial dehydrogenases by calcium ions. Biochim. Biophys. Acta. 1787, 1309-1316.

65 Balaban, R. S. (2009) The role of Ca(2+) signaling in the coordination of mitochondrial ATP production with cardiac work. Biochim. Biophys. Acta. 1787, 1334-1341.

66 Bround, M. J., Wambolt, R., Luciani, D. S., Kulpa, J. E., Rodrigues, B., Brownsey, R. W., Allard, M. F. and Johnson, J. D. (2013) Cardiomyocyte ATP production, metabolic flexibility, and survival require calcium flux through cardiac ryanodine receptors in vivo. J. Biol. Chem. 288, 18975-18986.

67 Elrick, M. J., Yu, T., Chung, C. and Lieberman, A. P. (2012) Impaired proteolysis underlies autophagic dysfunction in Niemann-Pick type C disease. Hum. Mol. Genet. 21, 4876-4887.

68 Lim, J. A., Li, L., Kakhlon, O., Myerowitz, R. and Raben, N. (2015) Defects in calcium homeostasis and mitochondria can be reversed in Pompe disease. Autophagy. 11, 385-402.

69 Jennings, J. J., Jr., Zhu, J. H., Rbaibi, Y., Luo, X., Chu, C. T. and Kiselyov, K. (2006) Mitochondrial aberrations in mucolipidosis Type IV. J. Biol. Chem. 281, 39041-39050.

70 Settembre, C., Fraldi, A., Jahreiss, L., Spampanato, C., Venturi, C., Medina, D., de Pablo, R., Tacchetti, C., Rubinsztein, D. C. and Ballabio, A. (2008) A block of autophagy in lysosomal storage disorders. Hum. Mol. Genet. 17, 119-129.

71 Ghislat, G., Patron, M., Rizzuto, R. and Knecht, E. (2012) Withdrawal of essential amino acids increases autophagy by a pathway involving Ca2+/calmodulin-dependent kinase kinase-beta (CaMKK-beta). J. Biol. Chem. 287, 38625-38636.

72 Grotemeier, A., Alers, S., Pfisterer, S. G., Paasch, F., Daubrawa, M., Dieterle, A., Viollet, B., Wesselborg, S., Proikas-Cezanne, T. and Stork, B. (2010) AMPK-independent induction of autophagy by cytosolic Ca2+ increase. Cell Signal. 22, 914-925.

73 Yu, T., Chung, C., Shen, D., Xu, H. and Lieberman, A. P. (2012) Ryanodine receptor antagonists adapt NPC1 proteostasis to ameliorate lipid storage in Niemann-Pick type C disease fibroblasts. Hum. Mol. Genet. 21, 3205-3214.
74 Sawkar, A. R., Adamski-Werner, S. L., Cheng, W. C., Wong, C. H., Beutler, E., Zimmer, K. P. and Kelly, J. W. (2005) Gaucher disease-associated glucocerebrosidases show mutation-dependent chemical chaperoning profiles. Chem. Biol. 12, 1235-1244.
75 Rigat, B. and Mahuran, D. (2009) Diltiazem, a L-type Ca(2+) channel blocker, also acts as a pharmacological chaperone in Gaucher patient cells. Mol. Genet. Metab. 96, 225-232.
76 Sun, Y., Liou, B., Quinn, B., Ran, H., Xu, Y. H. and Grabowski, G. A. (2009) In vivo and ex vivo evaluation of L-type calcium channel blockers on acid beta-glucosidase in Gaucher disease mouse models. PLoS One. 4, e7320.
77 Schultheis, P. J., Fleming, S. M., Clippinger, A. K., Lewis, J., Tsunemi, T., Giasson, B., Dickson, D. W., Mazzulli, J. R., Bardgett, M. E., Haik, K. L. et al. (2013) Atp13a2-deficient mice exhibit neuronal ceroid lipofuscinosis, limited alpha-synuclein accumulation and age-dependent sensorimotor deficits. Hum. Mol. Genet. 22, 2067-2082.
78 Fleming, S. M., Salcedo, J., Fernagut, P. O., Rockenstein, E., Masliah, E., Levine, M. S. and Chesselet, M. F. (2004) Early and progressive sensorimotor anomalies in mice overexpressing wild-type human alpha-synuclein. J. Neurosci. 24, 9434-9440.
79 Schindelin, J., Arganda-Carreras, I., Frise, E., Kaynig, V., Longair, M., Pietzsch, T., Preibisch, S., Rueden, C., Saalfeld, S., Schmid, B. et al. (2012) Fiji: an open-source platform for biological-image analysis. Nat. Methods. 9, 676-682.
80 Rogers, G. W., Brand, M. D., Petrosyan, S., Ashok, D., Elorza, A. A., Ferrick, D. A. and Murphy, A. N. (2011) High throughput microplate respiratory measurements using minimal quantities of isolated mitochondria. PLoS One. 6, e21746.
81 Xu, Y. H., Reboulet, R., Quinn, B., Huelsken, J., Witte, D. and Grabowski, G. A. (2008) Dependence of reversibility and progression of mouse neuronopathic Gaucher disease on acid beta-glucosidase residual activity levels. Mol. Genet. Metab. 94, 190-203.
82 Liou, B., Kazimierczuk, A., Zhang, M., Scott, C. R., Hegde, R. S. and Grabowski, G. A. (2006) Analyses of variant acid beta-glucosidases: effects of Gaucher disease mutations. J. Biol. Chem. 281, 4242-4253.
83 Sun, Y., Quinn, B., Witte, D. P. and Grabowski, G. A. (2005) Gaucher disease mouse models: point mutations at the acid beta-glucosidase locus combined with low-level prosaposin expression lead to disease variants. J. Lipid Res. 46, 2102-2113.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating an individual having neuronopathic Gaucher disease (nGD), comprising
    a) administering an effective amount of a ryanodine receptor inhibitor selected from dantrolene, JTV-519, flecainide-d3, flecainide, 4-(2-Aminopropyl)-3,5-dichloro-N,N-dimethylaniline (FLA 365), DHBP (1,1'-diheptyl-4,4'-bipyridium), ruthenium red (R2751), or a combination thereof, to said individual, wherein said administration is in an amount sufficient to reduce brain inflammation in said individual; and
    b) monitoring gait impairment in said individual during said treatment.

2. The method of claim 1, wherein said neuronopathic Gaucher disease is type II nGD.

3. The method of claim 1, wherein said neuronopathic Gaucher disease is type III nGD.

4. The method of claim 1, wherein said ryanodine receptor inhibitor is administered in an amount sufficient to reduce nGD associated autophagy, wherein said reduced autophagy is determined by reduced microtubule-associated protein 1A/1B-light chain 3 ("LC3-II") levels as compared to pre-treatment levels in said individual.

5. The method of claim 1, wherein said ryanodine receptor inhibitor is administered in an amount sufficient to improve mitochondrial function in said individual.

6. The method of claim 1, wherein said ryanodine receptor inhibitor is administered in an amount sufficient to improve sensory motor function in said individual.

7. The method of claim 1, wherein said ryanodine receptor inhibitor is administered in an amount sufficient to normalize ryanodine receptors (Ryrs) expression in said individual.

8. The method of claim 1, wherein said ryanodine receptor inhibitor is administered in an amount sufficient to reduce or normalize autophagy in said individual.

9. The method of claim 1, wherein said ryanodine receptor inhibitor is dantrolene.

10. The method of claim 1, wherein said ryanodine receptor inhibitor is a pharmaceutically acceptable salt of dantrolene, JTV-519, Flecainide-d3, Flecainide, 4-(2-

Aminopropyl)-3,5-dichloro-N,N-dimethylaniline (FLA 365), DHBP (1,1'-diheptyl-4,4'-bipyridium), Ruthenium red (R2751), or a combination thereof.

11. The method of claim 10, wherein said Gaucher disease is type II nGD.

12. The method of claim 10, wherein said Gaucher disease is type III nGD.

13. The method of claim 10, wherein said ryanodine receptor inhibitor is administered in an amount sufficient to reduce nGD associated autophagy, wherein said reduced autophagy is determined by reduced LC3-II levels as compared to pre-treatment levels in said individual.

14. The method of claim 10, wherein said ryanodine receptor inhibitor is administered in an amount sufficient to improve mitochondrial function in said individual.

15. The method of claim 10, wherein said ryanodine receptor inhibitor is administered in an amount sufficient to improve sensory motor function in said individual.

16. The method of claim 10, wherein said ryanodine receptor inhibitor is administered in an amount sufficient to normalize Ryrs expression in said individual.

17. The method of claim 10, wherein said ryanodine receptor inhibitor is administered in an amount sufficient to reduce or normalize autophagy in said individual.

* * * * *